(12) United States Patent
Cavallazzi

(10) Patent No.: US 9,707,025 B2
(45) Date of Patent: Jul. 18, 2017

(54) CABLE TENSIONER FOR A PERIPROSTHETIC REPAIR SYSTEM

(71) Applicant: Biomet C.V., Gibraltar (GI)

(72) Inventor: Cesare Cavallazzi, Miramar, FL (US)

(73) Assignee: Biomet C.V., Gibraltar (GI)

( * ) Notice: Subject to any disclaimer, the term of this patent is extended or adjusted under 35 U.S.C. 154(b) by 70 days.

(21) Appl. No.: 13/778,272

(22) Filed: Feb. 27, 2013

(65) Prior Publication Data

US 2014/0243841 A1 Aug. 28, 2014

(51) Int. Cl.
| A61B 17/80 | (2006.01) |
| A61B 17/88 | (2006.01) |
| A61B 17/17 | (2006.01) |
| A61B 17/74 | (2006.01) |
| A61B 17/82 | (2006.01) |

(52) U.S. Cl.
CPC ...... *A61B 17/8869* (2013.01); *A61B 17/1728* (2013.01); *A61B 17/74* (2013.01); *A61B 17/8014* (2013.01); *A61B 17/8061* (2013.01); *A61B 17/82* (2013.01)

(58) Field of Classification Search
CPC .................... A61B 17/885–17/8872; B65H 2515/31–2515/314
USPC ....... 606/86 B, 103–105, 280–299; 242/410, 242/412; 254/418–420, 100, 103
See application file for complete search history.

(56) References Cited

U.S. PATENT DOCUMENTS

| 5,116,340 | A | * | 5/1992 | Songer | A61B 17/8869 29/282 |
| 5,788,697 | A | * | 8/1998 | Kilpela | A61B 17/8869 254/199 |
| 5,902,305 | A | * | 5/1999 | Beger et al. | 606/103 |
| 7,250,054 | B2 | * | 7/2007 | Allen et al. | 606/74 |
| 8,133,235 | B2 | * | 3/2012 | Fritzinger | 606/103 |
| 8,469,966 | B2 | * | 6/2013 | Allen et al. | 606/103 |
| 2004/0199169 | A1 | * | 10/2004 | Koons et al. | 606/103 |

* cited by examiner

*Primary Examiner* — Jan Christopher Merene
*Assistant Examiner* — Steven Cotroneo
(74) *Attorney, Agent, or Firm* — Schwegman Lundberg & Woessner, P.A.

(57) ABSTRACT

A system, devices and methods are provided for facilitating stabilization of periarticular fractures. The system includes a compression plate and one or more of a cerclage cable for encircling the bone and securing the compression plate to the bone, a crimp lug for securing the cable in tension relative to the bone and/or a plate, and a supplemental plate coupled to the compression plate and adapted to receive bicortical or unicortical bone screws to further secure the compression plate relative to the bone. In addition, the system includes a cable tensioner for temporarily retaining the cable in tension and then applying a tension to the cable until a desired compression is effected between a plate and bone and while a cable retaining structure is secured to the cable to retain the applied tension on the cable. Also provided is a jig for use with plates for minimally invasive fracture stabilization.

18 Claims, 24 Drawing Sheets

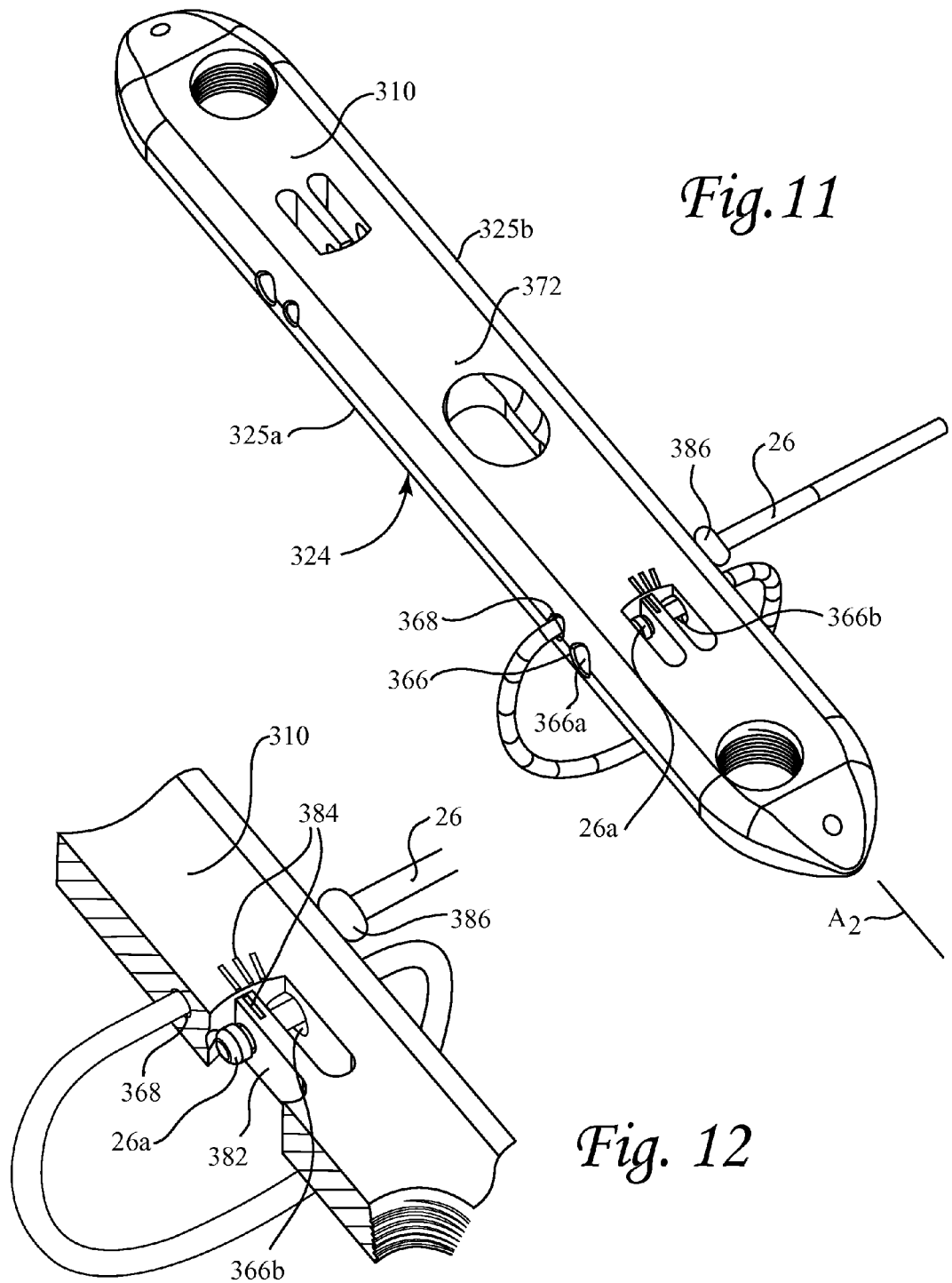

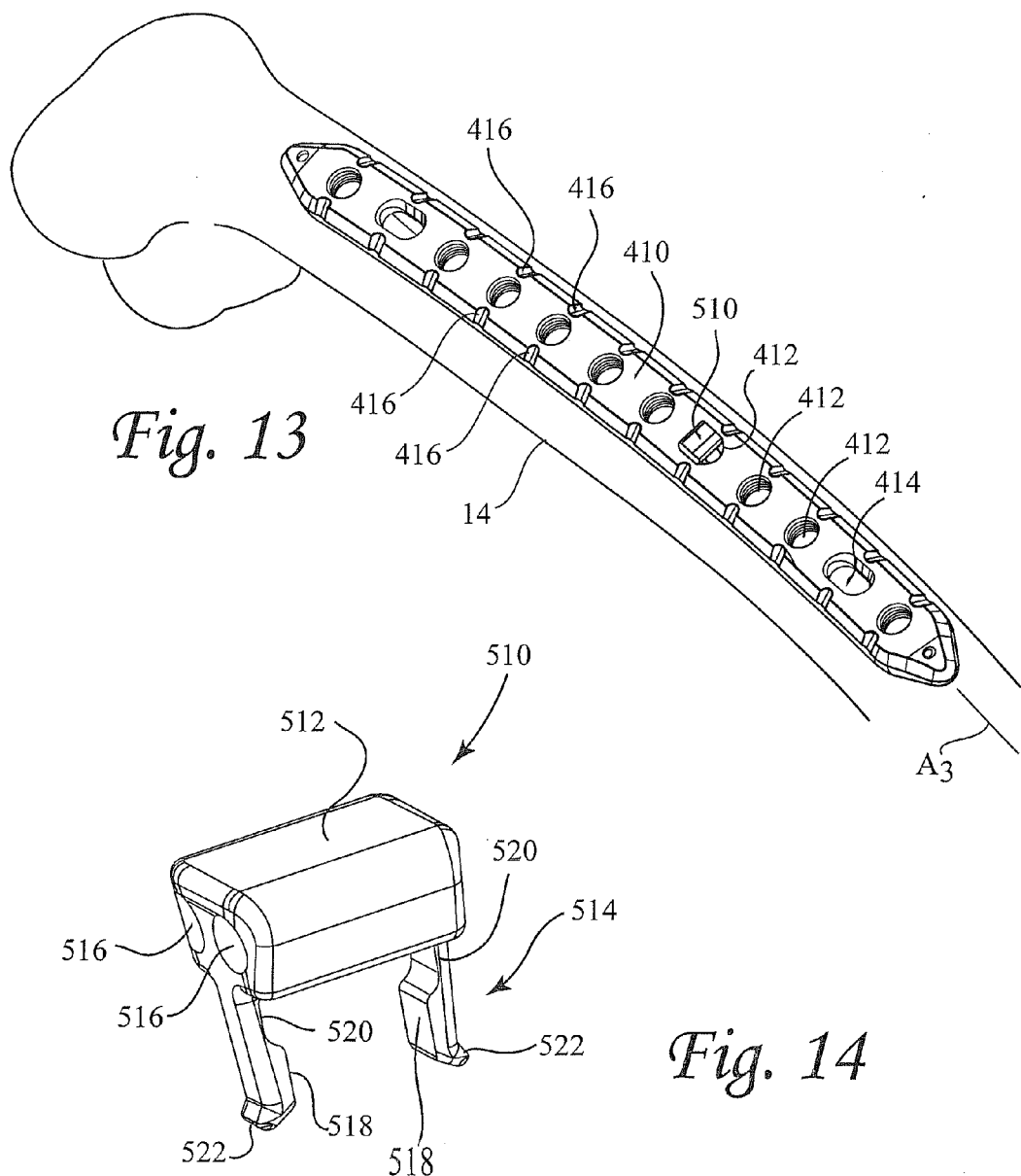

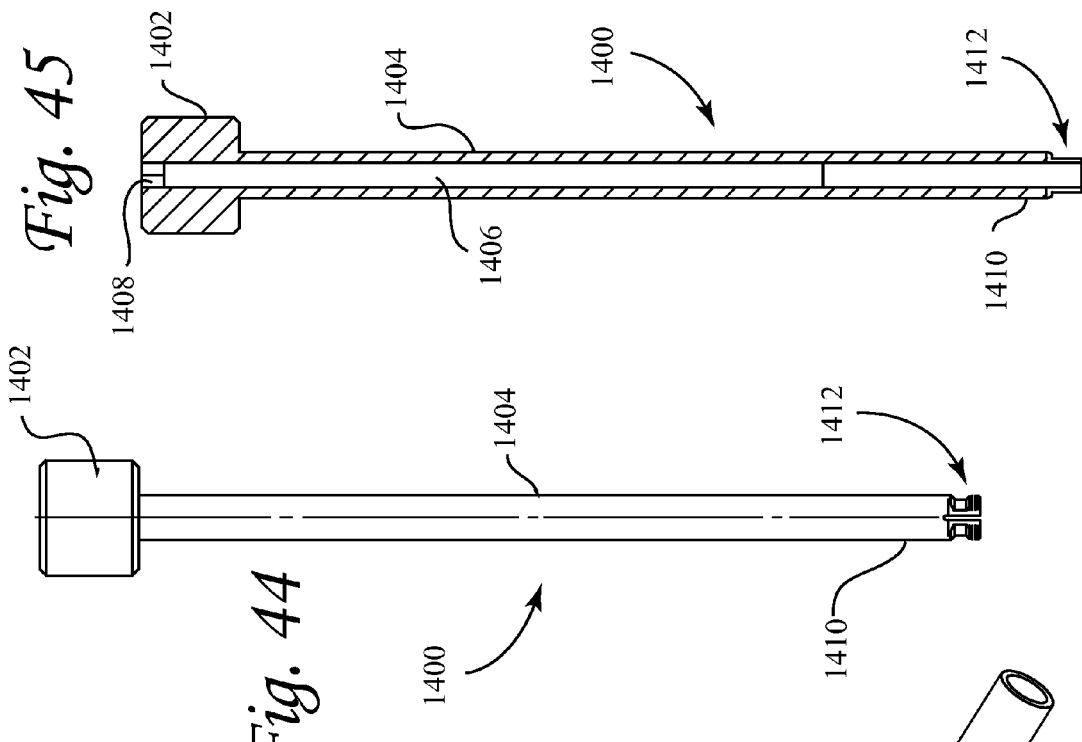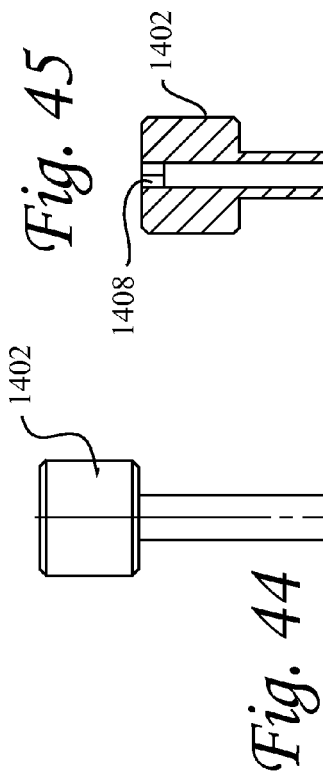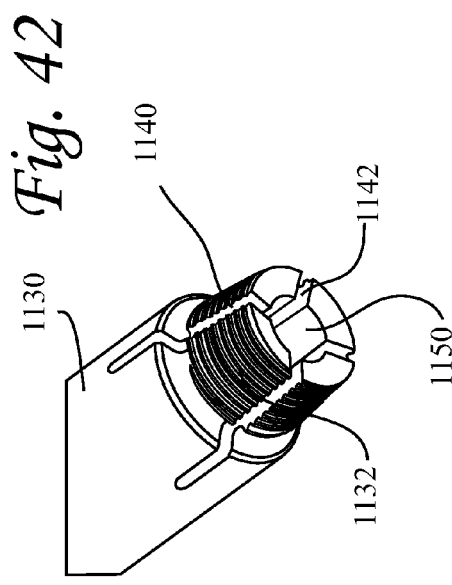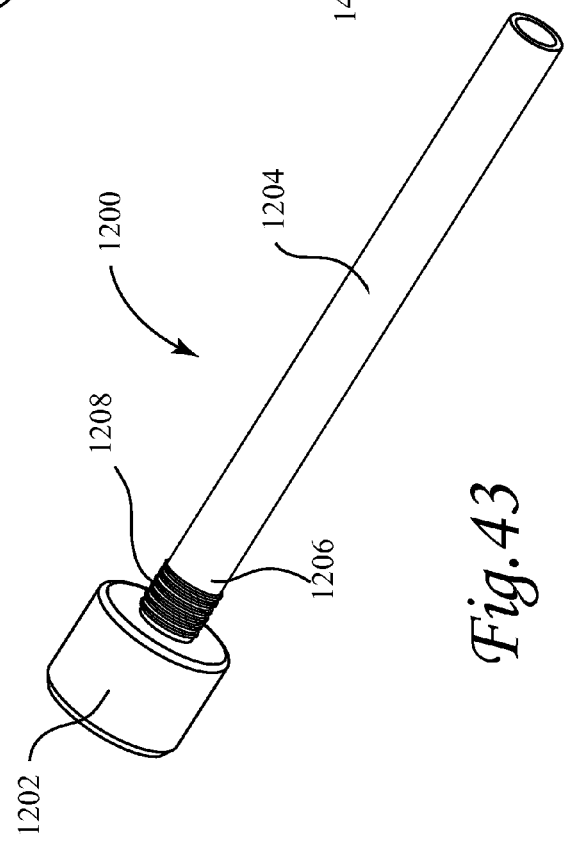

CABLE TENSIONER FOR A PERIPROSTHETIC REPAIR SYSTEM

BACKGROUND OF THE INVENTION

1. Field of the Invention

The present invention relates to surgery. More particularly, the present invention relates to plating systems and tools, and specifically plating systems and tools for treatment of periarticular fractures.

2. State of the Art

Fractures around implants pose unique fixation challenges. The original placement of the implant may predispose the bone to later fracture, as the long-term presence of the implant may change the structure of the surrounding bone and increase susceptibility to fracture. In addition, the implant itself may interfere with healing or the placement of other fixation devices.

This is particularly a problem around the femur where a femoral component of a hip replacement prosthesis may be implanted. Further, as the population ages and the indications for joint replacement increase, the number of implants in the femur is increasing. With increased hip joint replacement, the number of fractures associated therewith has also increased. Once a fracture occurs, treatment is complicated by osteoporosis, defects in the bone, and the presence of the implant. In particular, stems, rods, screws, and methylmethacrylate may block the medullary canal, preventing intramedullary fixation of fractures. Stems and rods also block screw fixation through the medullary canal to hold fracture stabilization plates on bone. The techniques for treating periprosthetic fractures are generally more difficult, with limited options.

Nevertheless, essentially all periprosthetic fractures require some treatment. Stable nondisplaced fractures may only require protected weight-bearing or cast/brace immobilization. However, most unstable periprosthetic implant fractures require surgical stabilization and/or implant replacement to restore function.

Surgical stabilization includes plating to secure the adjacent sections of the fractured bone to facilitate healing, which may occur with or without implant replacement.

It must be appreciated that standard plating includes attaching a stabilization plate to the bone with screws. Given the inability to pass a screw bicortically through the bone and the overall poor quality of the bone, alternative means of fixation are used to couple the plate to the bone. Most typically, such fixation includes unicortical screws that are inserted into the bone in a spatial distribution that does not interfere with the implant and cerclage cables that are wrapped under tension around the bone. The ends of the cable are crimped together with a crimp to maintain tension on the cable at a specific force. However, current tools for working with securing the cable make application of the system difficult. In particular, existing cable tensioners require a temporary tension holder as well as a separate cable tensioner, and both instruments must be operated together and used to tension the cable. In addition, after tension is applied and fixed to the cable, even a small amount of movement between the cable, the plate and the anatomy can cause significant reduction in tension on the cable and release of compression between the plate and the bone.

SUMMARY OF THE INVENTION

In accord with the invention, a system is provided for facilitating stabilization of periarticular fractures. The system includes a compression plate and a cerclage cable for encircling the bone and securing the compression plate to the bone. The cable has a ball or other structure functioning as a stop at one end, and a free end.

More particularly, the compression plate includes a plurality of screw holes preferably including at least one threaded screw hole extending between an upper surface of the plate and an opposing bone contacting lower surface of the plate, and at least one compression slot also extending between the upper and lower surfaces of the plate.

In one embodiment, the compression plate includes screw-receiving tabs that are configurable by the surgeon at the time of implantation. The tabs may be integrated with the plate. Additionally or alternatively, in accord with another preferred aspect of the invention, the system may also include one or more supplemental plates usable over the compression plate. The supplemental plates are short bent plates having a bridge portion with a screw hole, and which can be positioned in a transverse (lateral) configuration over the compression plate and secured thereto by insertion of a set screw through the hole in the supplemental plate and into threaded engagement with the compression plate therebelow. The supplemental plate has a plurality of screw-receiving tabs that are configurable by the surgeon at the time of implantation. In addition, the compression plate may be provided with a longitudinally displaced recesses on opposing lateral side of plate located in alignment with the threaded screw holes. When a supplemental plate is attached to the compression plate, portions of the supplemental plate fit into the recesses on the lateral sides of the plate to lock the orientation of the supplemental plate to the compression plate; i.e., prevent rotation of the supplemental plate relative to the compression plate.

In accord with another aspect of a compression plate according to the system, the compression plate includes an integrated cable securing structure. In an embodiment, the cable securing structure includes two cable passages extending in a widthwise direction through the plate. The first passage includes an opening of a sufficiently large diameter to permit a portion of the cable to pass therethrough. The second passage includes an opening of a sufficiently large diameter to permit a portion of the cable to pass therethrough but sufficiently small diameter to retain a ball end of the cable. In use, the cable is first fed through the second opening until the ball end of the cable is retained at the opening thereof, the cable is wrapped about the bone, the cable is inserted into the first passage and drawn into tension to cause the desired compression of the plate against the bone, and then a crimp is applied to the end of the cable extending through the first passage to retain the cable in tension relative to the plate. In accord with one aspect of the invention, the second passage is defined within a cantilevered resilient beam (deflection beam) that adds elasticity to the tensioned cable. The deflection beam is preferably paired with indicia on the plate such that the beam and indicia together indicate at least a relative amount of tension applied to the cable. The beam and indicia are preferably visible under fluoroscopy facilitating ascertainment of the cable tension both during and after the surgical procedure.

In another embodiment, the cable securing structure includes first and second passages extending widthwise through the plate and an integrated resilient clamp which can be clamped toward a closed position with a set screw adjacent the second passage to reduce the diameter of the second passage. The integrated resilient clamp preferably comprises a deflectable member unitary with the plate and which when clamped closed with the set screw to secure the cable preferably is not caused to exceed the elastic limits of the plate material and does not undergo plastic deformation. In use, the cable is first fed through the first passage until the ball end stops its progress, the cable is wrapped about the bone, the cable is inserted into the second passage and drawn into tension to cause the desired compression of the plate against the bone, and then the set screw is rotated to clampingly secure the cable relative to the plate.

In accord with another aspect of the invention, the system may include discrete crimp lugs formed separate from the plate and provided for guiding a cable, and securing the ends of the cable relative to each other in tension. Each crimp lug includes a head with two eyelets extending through a wall thickness of the lug, and a plate retaining feature that permits the positioning of the crimp lug within a screw hole of the compression plate. The retaining feature preferably permits a crimp lug to be retained through frictional interference, threading, or other mechanical interference with the plate at the screw hole. The retaining feature may be resiliently deformable for insertion into a screw hole. Before the ends of the cable are secured, a discrete crimp lug is self-engaged within a screw hole, and maintains such engagement regardless of the orientation of the plate and while the surgeon works to feed the cable through the eyelets. Once cable is advanced through the eyelets, the head of the crimp is plastically deformed to retain the cable in tension about the bone and plate.

In accord with yet another aspect of the invention, the system may include discrete crimp lugs formed separate from the plate and provided with retaining structure for attachment of the lug directly to the bone independent of a plate. Each such crimp lug includes a head with two eyelets extending through a wall thickness of the lug. The retaining structure is preferably a threaded shaft or a sharpened post, such as a tack end or nail end, each permitting the lug to be driven into the bone for temporary or permanent fixation. The lug can then be used in a standard manner, permitting cable ends to be advanced through the respective eyelets, drawn into tension about a plate and bone, and then retained in tension by plastic deformation of the head of the lug.

In addition, the system includes an instrument for tensioning a cable advanced through the eyelets of an integrated cable securing structure, a separate cable crimp lug, or used in association with any other structure for stabilization of a periarticular or other fracture. The cable tensioner is a single instrument having a proximal gear box and a distal tube. In a preferred embodiment the gear box includes a worm screw having a torque driver socket, the worm screw in gear-engagement to a drive gear, a cable pulley rotationally fixed to the drive gear, and a collet and a locking knob in rotational alignment and fixation relative to the pulley, such components together housed in or on a housing. The pulley has a plurality of grooves in the circumferential track of the pulley. The tube has a distal end pre-formed with a gentle curve and a proximal end secured at the housing.

In operation of the cable tensioner, no assembly of the cable tensioner is required nor is it required to be used with any other instrument component. The cable free end is passed through a first passage in the plate or eyelet of the crimp lug, positioned around the bone and then passed though the second passage or eyelet in the plate or crimp lug. The free end is then inserted into the curved distal end of the tension tube of the cable tensioner and advanced towards/through the cable tensioner housing. The free end of the cable is pulled and the cable tensioner is advanced towards the plate or crimp lug until the tensioner tube contacts the plate or crimp lug. The free end of the cable is then advanced around a portion of the pulley, through one of the grooves in the pulley, and then into the respective central holes of the pulley, the collet and the locking knob. The cable is manually pulled taught until there is no cable slack between the tube and the pulley. Then the locking knob is rotated until the cable is retained relative to the proximal housing of the tensioner. A driver is inserted into the worm screw end and engaged with a driver socket, and as the driver is rotated in a first direction the worm gear rotates to "spool" the cable onto the pulley. The portion of the cable extending around the bone decreases and compresses the plate onto the bone. Also, if the driver is rotated in an opposite second direction, the length of cable extending about the bone is increased, the tension on the cable is decreased, and the applied compression between the plate and bone is decreased. Once the cable tensioner is operated to apply the desired tension to the cable, the cable can be appropriately secured relative to the plate, lug, or other structure.

BRIEF DESCRIPTION OF THE DRAWINGS

FIG. 6 is a perspective view of a further grip-type compression plate in association with two different types of supplemental plates.

FIG. 11 is a perspective view of a compression plate with even yet another integrated cable retaining structure.

FIG. 12 is an enlarged partial section perspective view of a portion of FIG. 11.

FIG. 13 is a perspective view of another compression plate shown relative to a distal femur, and provided with a crimp lug.

FIG. 14 is a perspective view of one embodiment of a crimp lug.

FIG. 42 is a perspective view of a distal end of the locking guide for locking the jig relative to the bone plate.

FIG. 43 is a perspective of an outer sleeve for use with the jig of FIG. 40.

FIG. 44 is a side elevation of a drill guide for use with the jig of FIG. 40.

FIG. 45 is a longitudinal section view of the drill guide of FIG. 44.

DETAILED DESCRIPTION OF THE PREFERRED EMBODIMENTS

With reference to the human body and components of the system described herein which are intended to be implanted in the human body, the terms "proximal" and "distal" are defined in reference to the location at which a limb is connected to the torso, with the term "proximal" being the end of the limb, bone, or plate closer to the torso, and the term "distal" being the end of the limb, bone, or plate further from the torso. In addition, the term "lower" and "upper" in reference to plate surfaces are designations in which the lower surface is that surface closer to or seating on the bone, and the upper surface is that surface opposite the lower surface. Further, with respect to a plate, the terms "length", "width" and "thickness" are relatively transverse dimensions with the length being the dimension along the longitudinal axis of a plate, the width is a laterally transverse dimension to the length, and the thickness is a dimension extending between the upper and lower surface.

With reference to instruments of the system that are hand-held by a user, the terms "proximal" and "distal" are defined in reference to the user's hand, with the term "proximal" being closer to the user's hand, and the term "distal" being further from the user's hand.

In accord with the invention, a system is provided for facilitating stabilization of a periarticular fracture. The system includes a compression plate and one or more of the following: a cerclage cable for encircling the bone and securing the compression plate to the bone, a bicortical bone screw for extension from one side of the bone, through the medullary canal, and into the other side of the bone, and a unicortical bone screw for extension at least partly into the bone.

Figure 1:
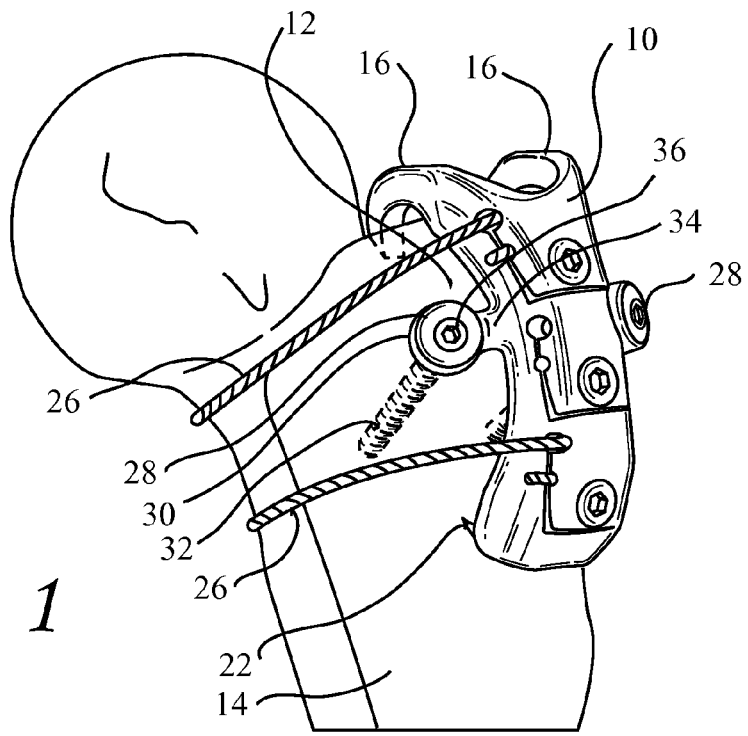
FIG. 1 is a perspective view of a short grip-type compression plate applied at the trochanter of the femur.
Figure 2:
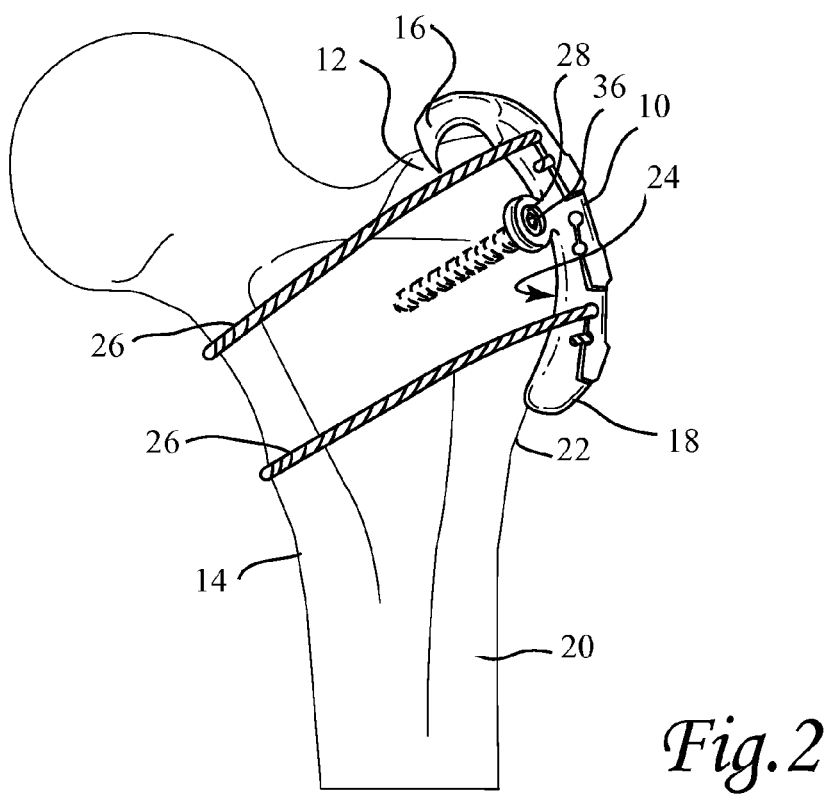
FIG. 2 is a side view of the grip-type compression plate of FIG. 1 applied at the trochanter of the femur.

Referring to FIGS. 1 and 2, one compression plate according to the system of the invention is a short grip plate 10. The short grip plate 10 is designed for placement over and reattachment of the greater trochanter 12 of the proximal femur 14 after the greater trochanter is removed in an osteotomy procedure. To secure the re-positioned greater trochanter to the remainder of the femur for proper healing, the proximal end of the grip plate includes hooks 16 that can be positioned around the greater trochanter and embedded into the femur bone using an impactor instrument (not shown). At a portion of the plate for placement at the inferior portion 18 of the greater trochanter (i.e., at or proximate the intersection with the diaphysis 20 of the femur) the plate preferably includes one or more spikes 22 at its lower surface 24 that can also be embedded in the bone to aid in at least temporary fixation of the plate on the femur, e.g., while the plate is more permanently secured to the bone with cerclage cables 26 and/or screws 36. The cables 26 are preferably non-elastic metal cables, constructed from, e.g., titanium, stainless steel or cobalt chrome, and encircle a portion of the bone 14, and placed under tension to apply a stabilizing compressive force between the plate and bone. The spikes 22 also provide rotational stability of the plate 10 on the bone even after the plate is secured by the cables 26. In fact, the tension on the cables 26 around the plate 10 and bone forcibly embeds the spikes 22 further into the bone for increased stability.

The short grip plate 10 includes a portion between the hooks 16 and spikes 22 in which the lower surface is concave in the longitudinal direction such that the plate accommodates the convex anatomy of the greater trochanter 12. In a shorter plate, as shown, such concave curvature may occur over substantially the entire length of the plate. In a longer grip plate, such as plate 10' shown in FIG. 3 and described below, such concave lower surface curvature is generally provided only along the proximal portion of the plate, with the remainder of the plate substantially straighter to conform to the diaphyseal portion of the femur.

In accord with one aspect of the invention, the grip plate 10 includes at least one pair of screw tabs 28 extending transversely from the opposing (lateral) sides of the plate. The screw tabs 28 each include a ring 30 defining a threaded screw hole 32 attached to the plate by a bendable bridge 34. The threaded screw hole is for receiving and engaging the threaded head of bone fastener 36. The tabs 28 can be bent about the bridges 34 and thereby manipulated in orientation either before or after the plate is positioned on the bone by using drill guides installed in threaded screw holes of the rings, as described in detail in U.S. Pat. Nos. 7,935,126 and 8,192,472, and US Pub. No. 20100069966A1, each of which are hereby incorporated by reference herein in their entireties. This allows the axial orientation of the screw hole to be customized for the particular fixation and particularly based on the location of the osteotomy, the medullary canal content, or other considerations.

Figure 3:
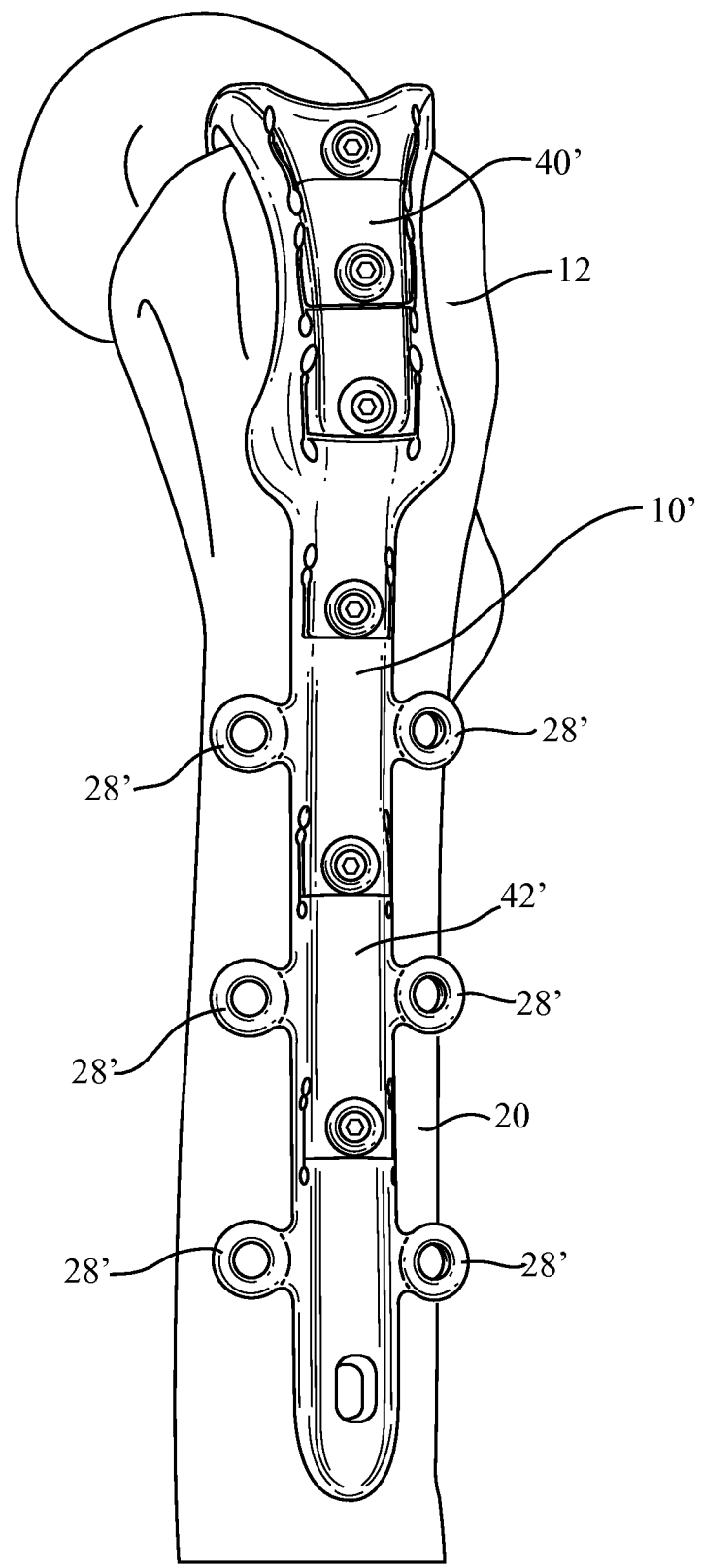
FIG. 3 is a front view of another grip-type compression plate located on a femur.

The grip plate 10 can be provided in several sizes and lengths. As discussed, FIGS. 1 and 2 illustrate a short grip plate used locally about the greater trochanter. For trochanters of different sizes, plates can be provided in having a range of dimensions between the proximal hooks. Referring to FIG. 3, a longer grip plate 10' is shown which includes a proximal head 40' for placement at the trochanter 12 and a distal shaft 42' adapted for extension along the diaphysis 20 of the femur. The plate shaft 42' includes a plurality of pairs of aligned screw tabs 28' extending transversely from opposing sides of the plate which function in a similar manner to screw tabs 28. That is, each screw tab 28' has a threaded hole for receiving and engaging the threaded head of bone fastener. In addition, the screw tabs 28' are preferably reconfigurable with the use of drill guides as discussed above. It is within the scope of the invention to provide a plate that includes screw tabs both along the head and shaft of the bone plate, thus combining features of plates 10 and 10'.

Figure 4:
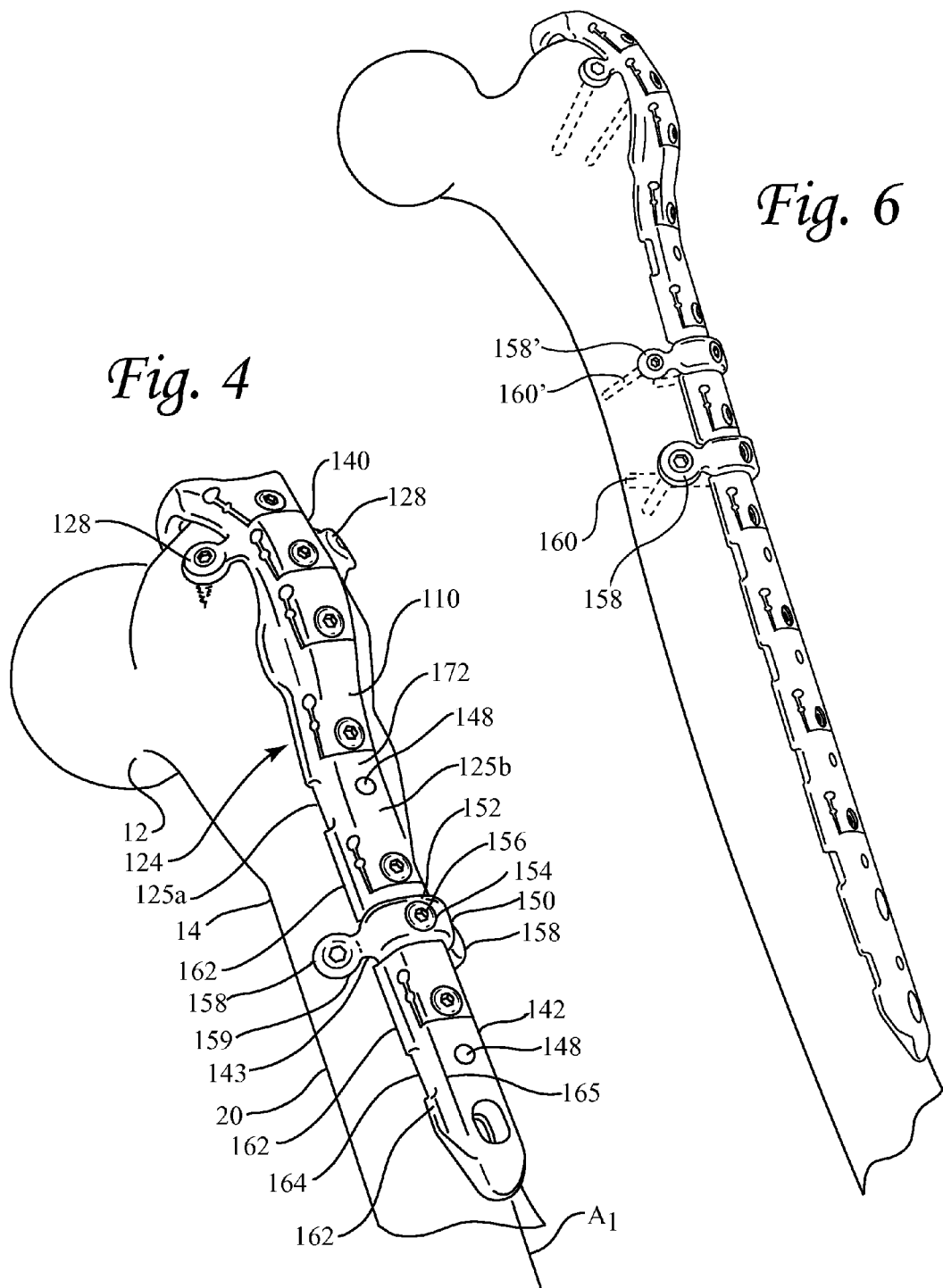
FIG. 4 is a perspective view of yet another grip-type compression plate in association with supplemental plates.

Turning now to FIG. 4, another embodiment of a grip plate 110, generally similar to plates 10, 10', is shown. Grip plate 110 is a long plate having tabs 128 at its head portion 140 for engagement with the trochanter 12 and an elongate shaft 142 for extension along the diaphysis 20 of the femur 14. The grip plate 110 includes a longitudinal axis $A_1$, upper and lower surfaces 172, 124, and opposing longitudinal sides 125a, 125b extending between the upper and lower surfaces. The grip plate includes a plurality of longitudinally spaced apart threaded screw holes 148 along its shaft 142. In accord with another aspect of the invention, the grip plate 110 includes one or more supplemental plates 150 positioned over and couplable to the grip plate 110 at the threaded screw holes. Each supplemental plate 150 is a short bent 'bridge' plate having an upper portion 152 and first and second lower portions 143 each with screw receiving tabs 158. The bridge plate 150 can be positioned in a transverse (lateral) configuration over the compression plate 110, and the upper portion 152 is provided with a screw hole 154 at which it can be secured to the compression plate by insertion of a set screw 156 through hole 154 and into the threaded hole 148 of the compression plate 110 therebelow. The threaded hole 148 is preferably tapered. The set screw 156 preferably has a tapered collet-like split shaft, such that when the set screw 156 is advanced into the screw hole 148, it can collapse in a radial direction to facilitate locking relative to compression plate 110. The screw-receiving tabs 158 at the lower portions include preferably threaded holes for receiving a bone screw with a threaded head or a non-threaded head, and are bendable about a reduced width span 159 such that the axial orientation of the threaded holes can be reconfigured by the surgeon at the time of implantation, e.g., with the drill guides referenced above. As shown in FIG. 6, supplemental plates may be provided with larger tabs 158 for receiving larger headed screws, such as provided with bicortical screws 160 that can extend across the cortex of the diaphysis, or smaller tabs 158' for receiving the smaller headed screws, such as unicortical screws 160', or a combination of supplemental plates to accommodate both types and various sizes of screws. Supplemental plates with such different tab sizes can be coupled at different threaded holes of the compression plate. As seen best in FIGS. 4 and 5, the plate 110 is preferably provided with a peripheral lip 162 extending along the opposing sides 125a, 125b adjacent the lower surface 124 of the plate, with such lip provided with interruptions 164 located in alignment with threaded screw holes 148 that define recesses 165 along the sides of the plates. The interruptions 164 have a length corresponding to the widthwise dimension of the supplemental plate across the lower portions 143. When a supplemental plate 150 is attached to the compression plate, the lower portions 143 of the supplemental plate 150 fit between the interruptions 164 such that the lip 162 surrounds the supplemental plate at proximal and distal sides thereof to further lock the rotational orientation of the supplemental plate 150 relative to the grip plate 110. Even without a lower lip, such lateral locking recesses 165 can be defined in the sides of the plate, as shown in FIG. 7.

Figure 5:
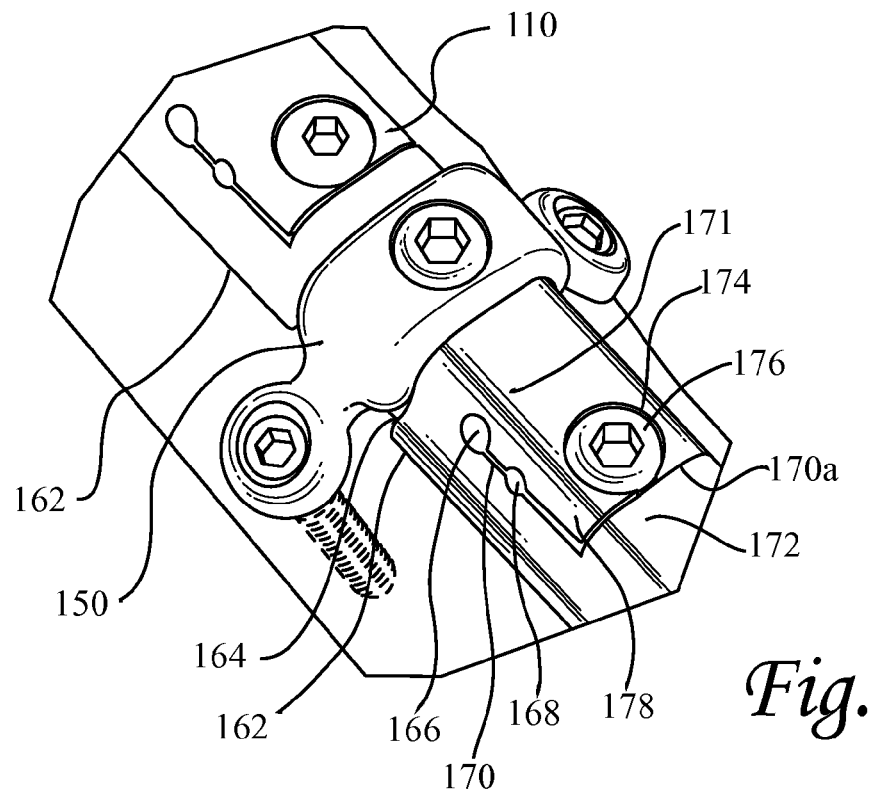
FIG. 5 is an enlarged perspective view of a portion of the shaft of the compression plate of FIG. 4, illustrating a supplemental plate and an integrated cable retaining structure.
Figure 7:
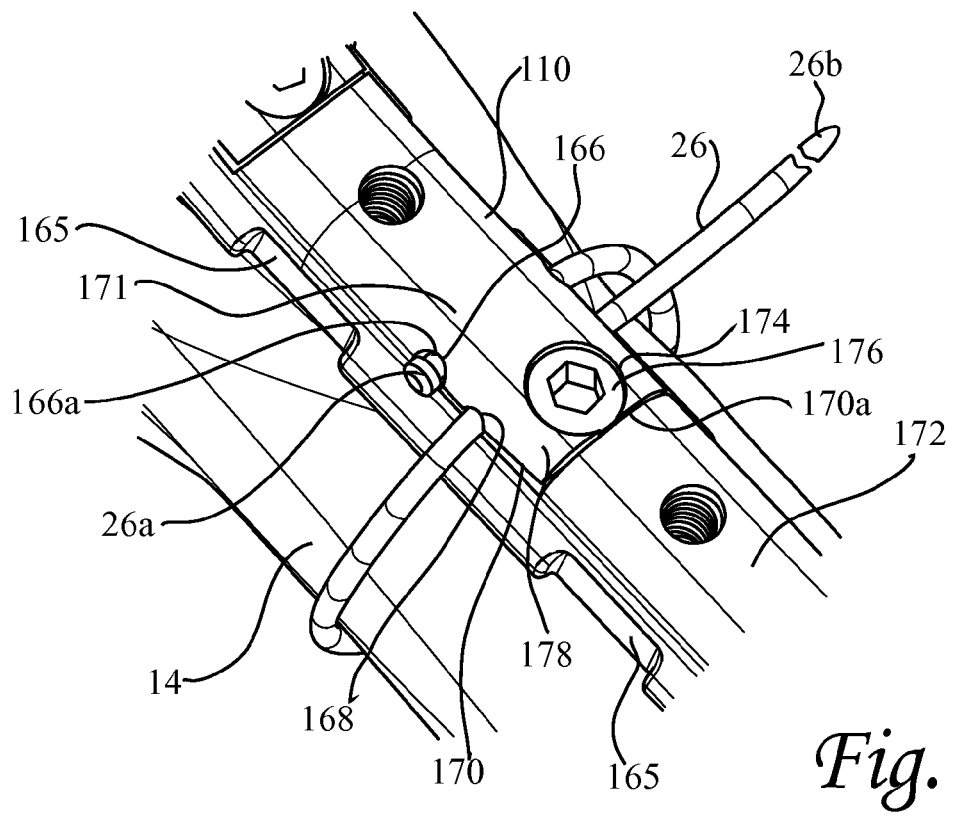
FIG. 7 is a view similar to FIG. 6, illustrating a cerclage cable within the integrated cable retaining structure and with the supplemental plate removed.
Figure 8:
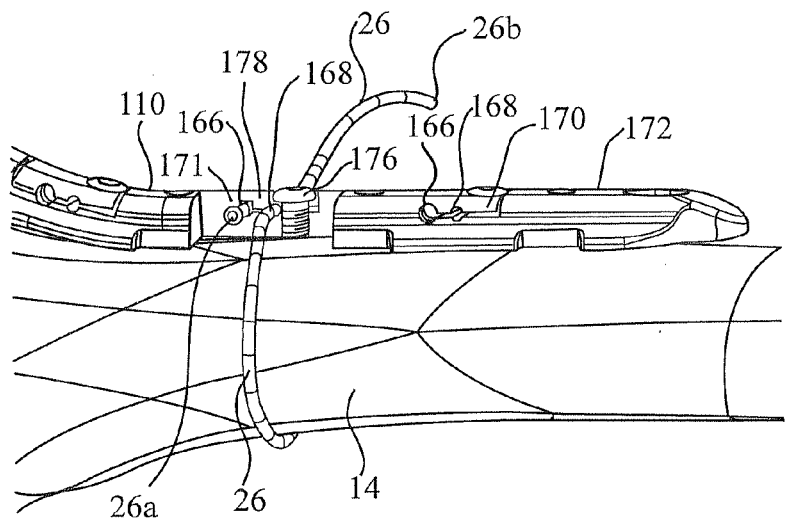
FIG. 8 is a side elevation view with a partial section of the plate with cable of FIG. 7.

Turning now to FIGS. 5, 7 and 8, the compression plate 110 includes an integrated cerclage cable securing structure. The cerclage cable 26 has a ball 26a or other structure functioning as a stop at one end, and an opposite free end 26b. The plate 110 has two transverse cable passages 166, 168 extending through the width of the plate. The first transverse passage 166 allows passage of the free end but restricts passage of the stop end 26a of the cable 26. The second transverse passage 168 also allows passage of the free end 26b of the cable therethrough. A slot 170 is provided within the plate 110 extending through the second passage 168 and into the first passage 166. The slot 170 also opens up to the upper surface 172 of the plate at 170a. As such, the slot 170 defines a gap between the upper plate surface 172 and the portion of the plate beneath the slot 170. The slot 170 may be formed, e.g., via laser or electric discharge machining (EDM). The plate at the end of the slot opposite open end 170a, i.e., over the first passage 166, defines a dynamic hinge 171 at one end of the gap. A set screw hole 174 is defined through the upper plate surface, 172, the slot 170, and the portion of the plate beneath the slot 170, at a location between where the slot opens at 170a to the upper surface 172 and the second passage 168; i.e., it is longitudinally offset from the second passage 168. The portion of the set screw hole 174 beneath the slot 170 is threaded. A set screw 176 is partially threaded into the set screw hole 174. A dynamically hinged clamp 178 is thus formed. As the set screw 176 is rotated, the diameter of the second passage 168 is modified in dimension, with seating the set screw 176 causing the clamp 178 to decrease the gap and close down on the second passage 168. While the hinge clamp 178 preferably is deformable about a dynamic hinge defined at the first transverse passage 166, in an alternate construction, the hinge may be defined via a different through passage. By way of example, a hinge through passage may be longitudinally displaced between the first and second passages 166, 168.

In use, the cable 26 is first fed through the first passage 166 until the ball end 26a of the cable is retained at the opening 166a thereof. The opening 166a of the first passage 166 may include a countersink to at least partially recess the ball end 26a. The free end 26b of the cable is then circled about the bone 14, and inserted into and through the second passage 168. The cable 26 is drawn into tension, preferably using the instrument 710 described below (FIGS. 20-22), such that the desired compression of the plate 110 against the bone 14 is provided, and then the partially seated set screw 176 is fully driven down against the hinge clamp 178 to cause the hinge clamp to impinge on the cable 26 and secure the cable at the desired tension.

Figure 9:
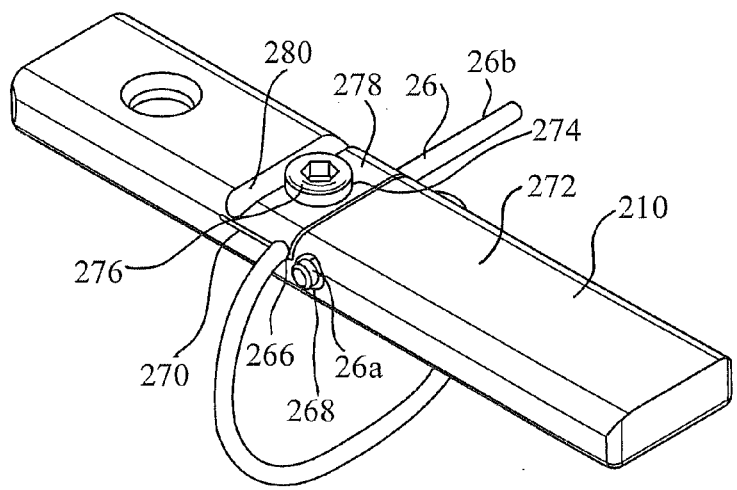
FIG. 9 is a perspective view of a compression plate with another integrated cable retaining structure and cable retained therein.
Figure 10:
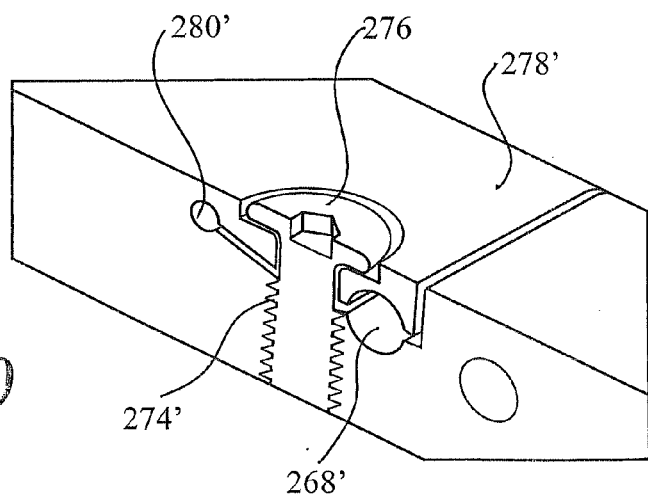
FIG. 10 is a perspective section view of a compression plate with yet another integrated cable retaining structure.

Turning now to FIG. 9, a compression plate 210 is shown with another integrated cerclage cable securing structure. The plate 210 has two transverse cable passages 266, 268 extending through the width of the plate 210. The first transverse passage 266 allows passage of the free end 26b but restricts passage of the stop end 26a of the cable 26. The second transverse passage 268 also allows passage of the free end 26b therethrough. A slot 270 is provided within the plate extending through the second passage 268 but preferably terminating short of the first passage 266. At a first end of the slot 270, the slot extends up to the upper surface 272 of the plate. The plate material is reduced at the upper surface over the second end of the slot 270 to define a dynamic hinge that is elastically deformable; i.e., to result in a hinge clamp 278. According to one such structure, a transverse groove 280 is formed in the upper surface of the plate, thus defining a dynamic hinge for a hinge clamp. Alternatively, as shown in FIG. 10, the material thickness may be reduced below the plate surface, e.g., with an enlarged transverse hole 280', to define the elastically deformable hinge clamp 278'. Referring to both FIGS. 9 and 10, between the first and second ends of the hinged clamp 278, 278', a set screw hole 274, 274' is defined within the hinge clamp and plate portion therebeneath, with the portion therebeneath being threaded. A set screw 276 is partially threaded in the set screw hole. As the set screw 276 is advanced, the hinge clamp 278, 278 impinges on the space of the second passage 268, 268'.

Referring generally to FIG. 9, in use, the cable 26 is first fed through the first passage 266 until the ball end 26a of the cable is retained at the opening thereof. The free end 26b of the cable is then circled about the bone (not shown), and inserted into and through the second passage 268. The cable 26 is drawn into tension, preferably using the instrument 710 described below (FIGS. 20-22), such that a desired compressive force between the plate and bone is obtained, and then the partially seated set screw 276 is fully driven down to cause the hinge clamp 278 to reduce the transverse dimension of the second passage and thereby impinge on the portion of the cable 26 within the second passage 268 such that the cable is secured at the desired tension. The flexing limits of the hinge portion of the hinged clamp (i.e., that portion under the transverse groove 280 (FIG. 9) or above the enlarged transverse hole 280' (FIG. 10)) remains within the elastic limits of the plate material and does not undergo plastic deformation when the set screw 276 is fully driven down to secure the cable.

Turning now to FIGS. 23 through 26, a compression plate 810, substantially similar to plate 210 (with like reference incremented by 600 corresponding to similar structure), is shown with the same or substantially similar integrated cerclage cable securing structure as shown with respect to the plate 210. The plate 810 defines first and second transverse cable passages 866, 868 extending through the width of the plate. The first transverse passage 866 extends under the hinge clamp 878 as described above. The second passage 868 is a stepped diameter bore extending through the plate at a longitudinally displaced location from the hinge clamp 878. The cerclage cable 826 includes a ball end 826a, and a compression coil spring 879 is provided about the end of the cable and in abutting contact with the ball end 826a. Alternatively, the spring may be different type of spring, such as a leaf spring or a Belleville washer, and additionally the spring may be installed in the second passage before the insertion of cable 826 therethrough. When the cable 826 is advanced through the second passage 868, the ball end 826a and spring 879 are retained in a larger diameter portion 868a of the passage 868, and the cable 826 continues through a smaller diameter portion 868b of the plate. The cable is then circled about the bone (not shown), and inserted into and through the second passage 866 and drawn into tension, resulting in compression of the spring 879, preferably using the instrument 710, 710' described below (FIGS. 20-22, 29-30), preferably until a desired compressive force between the plate and bone with spring compression is obtained. That is, the spring 879 is adapted to compress in proportion to the tension applied to the cable 826. Then, a crimp 886 is applied to the free end 826b of the cable adjacent the side of plate 810 to secure the tension on the cable. Alternatively or additionally, the free end may be secured with a dynamic hinge clamp integrated with the plate as described above and as shown in FIGS. 5 through 10. Once the tension is secured, the remaining cable beyond the plate and/or crimp 886 may be cut free. The spring 879 on the cable provides a degree of elasticity to the fixation that is not otherwise present in the assembly of the plate to the bone. Thus, in the event of micromotion, minor movement, or even slippage of the cable 826 on the bone or relative to the plate, the construct will continue to maintain tension to support the bone throughout the healing process.

Turning now to FIGS. 11 and 12, a compression plate 310, substantially similar to plate 210, is shown with another integrated cerclage cable securing structure. The plate includes a lower surface 324, an upper surface 372, sides 325a, 325b extending between the upper and lower surfaces, a length along said sides defining longitudinal axis $A_2$, a height extending between the upper and lower surface, and a width transverse to the length and the height. The plate 310 defines first and second transverse cable passages 366, 368 extending through the width of the plate. The first transverse passage 366 includes outer portions 366a, 366b that allow passage of both the free and stop ends of the cable, and an interposing centrally displaced cantilevered deflection beam 382 (preferably extending along the longitudinal axis $A_2$) that restricts passage of the stop end 26a of the cable. The deflection beam 382 is adapted to deflect in proportion to the tension applied to the cable 26. In addition, the deflection beam 382 is preferably paired with indicia 384 on the beam and/or the plate such that the beam 382 and indicia 384 together indicate at least a relative amount of tension applied to the cable 26 as the beam 382 is displaced or flexed through applied tension. The beam 382 and indicia 384 are preferably visible under fluoroscopy so that the relative cable tension can be ascertained during the surgical procedure, and even after the surgical wound has been closed and at any time post-operatively.

In use, the cable 26 is advanced through the first passage 366 until the stop 26a engages the deflection beam 382. The free end 26*b* of the cable is then circled about the bone (not shown), and inserted into and through the second passage 368. The cable is drawn into tension, preferably using the instrument 710 described below (FIGS. 20-22), until a desired compressive force between the plate and bone is obtained. Then, a crimp 386 is applied to the free end 26*b* of the cable adjacent the side of plate 310 to secure the tension on the cable. Alternatively, the plate may additionally be provided with an integrated hinged clamp, as described above, or other integrated securing element for securing the free end of the cable, such that, e.g., a set screw can be advanced to impinge on the cable and secure the cable at the desired tension. Once the tension is secured, the remaining cable beyond the crimp 386 may be cut free.

With the integrated deflection beam 382, the surgeon is able to visually determined the tension force on the cable by inspecting the amount of deflection imparted to the beam 382, and can adjust the tension accordingly. This is, of course, enabled without increasing the height profile of the plate 310 (between lower and lower surfaces 324, 372) or cable 26. In addition, the cable 26 is provided with a degree of elasticity that it is not inherently part of its construction. Thus, in the event of micromotion or minor slippage of the cable 26 on the bone or relative to the plate, the construct will continue to maintain tension to support the bone throughout the healing process.

Referring now to FIGS. 13 through 17, in accord with another aspect of the invention, the system includes discrete crimp lugs 510 for use with a compression plate 410. The plate 410 shown is a midshaft plate, but the following is applicable to any plate suitable for use in periprosthetic fracture fixation. The crimp lugs 510 are provided for guiding and securing the ends of a cable relative to each other in tension about the plate 410 and bone 14. The plate 410 preferably includes a plurality of a longitudinally displaced threaded holes 412 and one or more longitudinal compression screw slots 414. In alignment with each of the threaded holes and slots 412, 414 are transverse grooves 416 adapted in size (depth and diameter) for stabilized guidance of a cable in a direction transverse to a longitudinal axis $A_3$ of the plate 410 and bone 14.

Each crimp lug 510 includes a head 512 and a retaining feature 514 that permits the positioning of the crimp lug within a screw hole 412, 414 of the plate. Most preferably, the crimp lugs are attached relative to the threaded screw holes 412 and thus the retaining feature is adapted for engagement therein; however, the crimp lugs can be adapted for attachment at non-threaded round screw holes or non-circular screw slots.

The head 512 includes two eyelets 516 extending through a wall thickness of the lug, wherein the wall thickness extends in a dimension parallel to the transverse grooves 416 when a lug 510 is attached to the plate 410. The eyelets 516 are preferably sized to retain a stop 26*a* at the end of the cable 26 but to permit feeding the free end 26*b* of the cable therethrough. While the crimp lug 510 is preferably made as a unitary piece from a single material, it can be a composite structure. At least the head 512 is made from titanium or cobalt chrome or another material that can be collapsed on a cable 26 within the eyelets 516 with sufficient force to prevent cable pullout therefrom.

Figure 15:
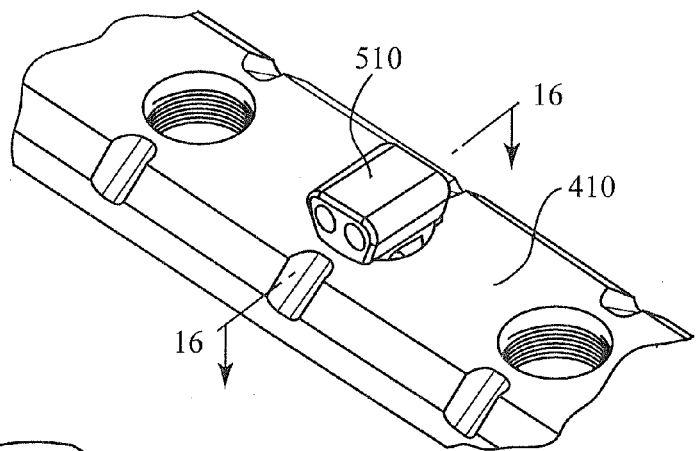
FIG. 15 is a perspective view of the crimp lug of FIG. 14 inserted into a screw hole in the compression plate of FIG. 13.
Figure 16:
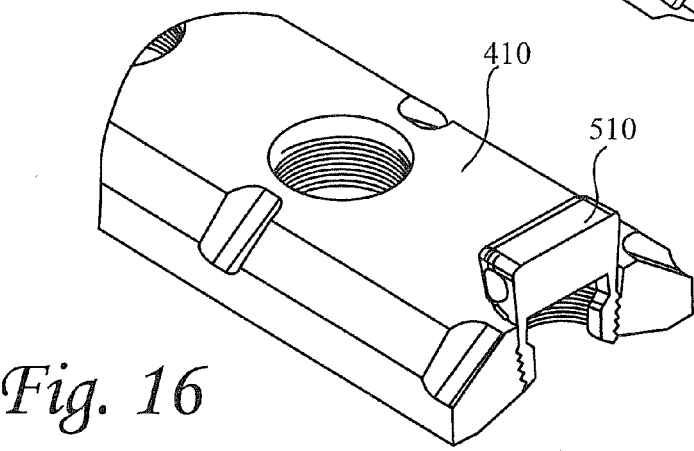
FIG. 16 is a transverse section view through line 16-16 in FIG. 15.

Referring to FIGS. 14 through 16, in one embodiment, the retaining feature 514 includes a pair of legs 518, each having a reduced upper thickness portion 520 about which they can resiliently articulate, resiliently bend, or otherwise resiliently deform. The lower end of each of the legs includes an outwardly extending foot portion 522 that is adapted to capture the plate at underside of a screw hole. Other possible retaining features for the at least temporary coupling the crimp lugs to the plate include: corresponding shapes between the retaining structure and the holes, corresponding dimensions adapted for frictional interference with the threaded or slot holes, non-resilient, plastically deformable structure insertable into the holes, external threads for threading with the threaded holes, or other structure permitting mechanical interference between the lug and the plate at the screw hole.

Figure 17:
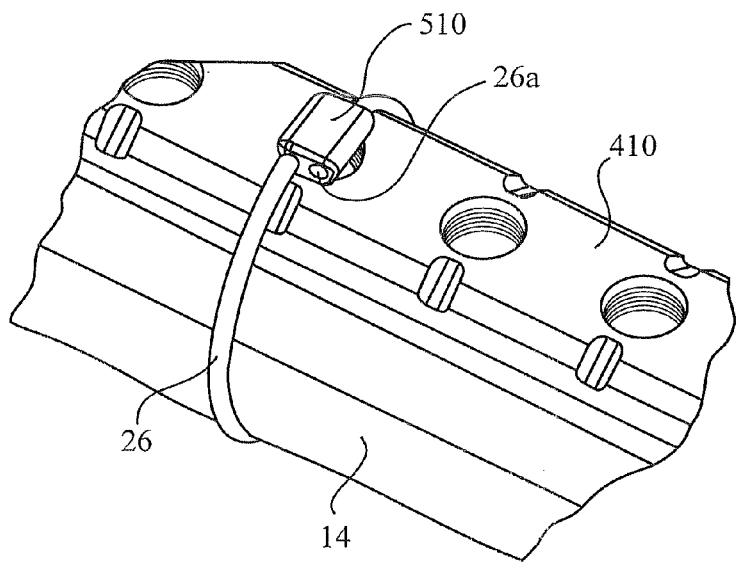
FIG. 17 illustrates the crimp lug securing a cerclage cable.

In use, an independent and discrete crimp lug 510 is positioned within a screw hole 414. In view of the mechanical interference between the crimp lug 510 and plate 410, the crimp lug 510 is coupled to the plate 410 as the surgeon handles the plate, regardless of the orientation of the plate, and further while the surgeon subsequently feeds cable 26 through the eyelets 516 of the crimp lug 510. The cable 26 is placed under tension and the lug is then plastically deformed about the cable (as shown in FIG. 17) to retain the tension, e.g., with a pliers. Then the remaining cable is cut and removed.

Figure 18:
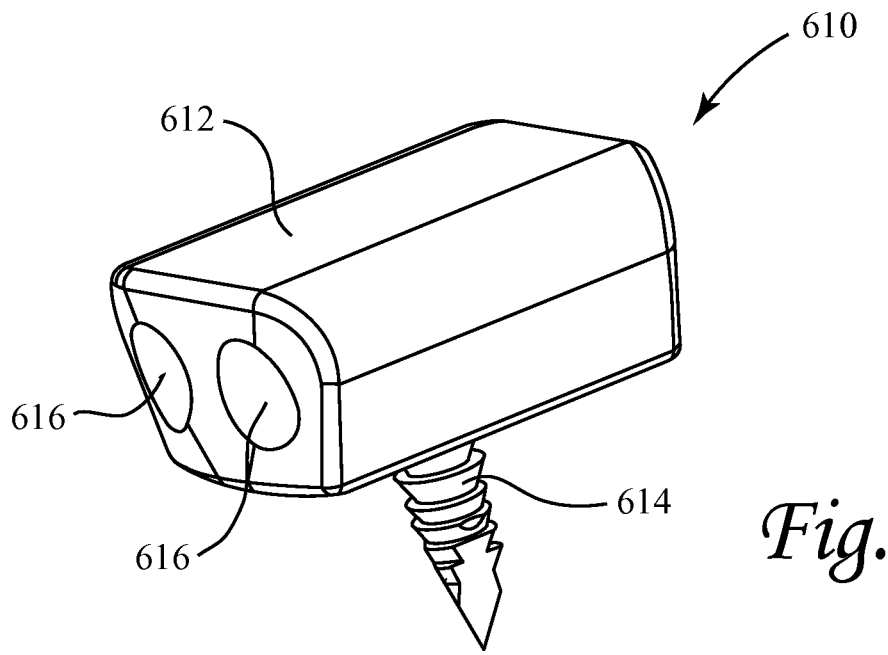
FIG. 18 is a perspective view of a first embodiment of a crimp lug for implantation in bone.
Figure 19:
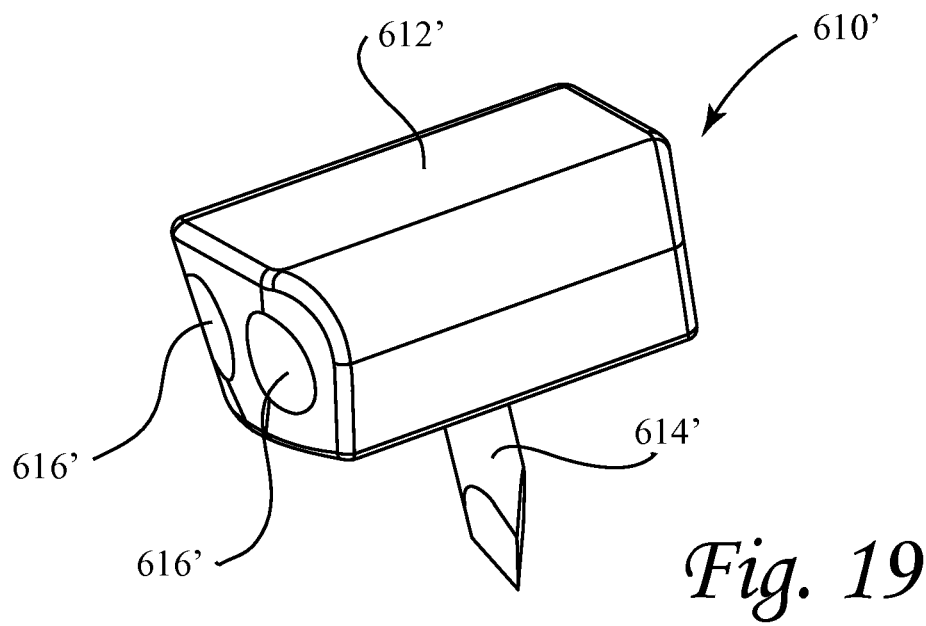
FIG. 19 is a perspective view of a second embodiment of a crimp lug for implantation in bone.

There may be instances in which it is desirable to guide and secure a cerclage cable about a bone independent of a bone plate. Turning now to FIGS. 18 and 19, in accord with yet another aspect of the invention, the system includes independent and discrete crimp lugs 610, and 610', provided with retaining features for attachment of the respective lugs relative to the bone independent of a plate. Crimp lug 610 (FIG. 18) includes a plastically deformable preferably trapezoidal head 612 with two eyelets 616 extending through a wall thickness of the lug, as described with respect to crimp lug 510. While the preferred shape of the head 612 is trapezoidal, as such accommodates the eyelets in a low profile on the bone or in the plate and is readily deformable to retain the cable, it is appreciated that the retainer can be provided with a head of another shape. The retaining feature is a barbed tack 614. Crimp lug 610' (FIG. 19) includes a substantially similar head 612' provided with a retaining feature of a sharpened smooth nail end 614', also permitting the lug to be driven into the bone for temporary or permanent fixation. In each of the embodiments of FIGS. 18 and 19, the heads 612/612' of the lugs 610/610' may have increased rigidity in axial direction (parallel to the extension of the post) such that it can be driven into the bone without significant deformation of the eyes 616/616', and then only after the cable has been advanced through the eyes and placed under the tension, the lug is deformed by plastic deformation of the head, preferably via application of a deformation force in a widthwise direction to the lug. As yet another alternative, the retaining feature may include a threaded shaft with preferably self-tapping threads adapted for insertion into bone.

Figure 27:
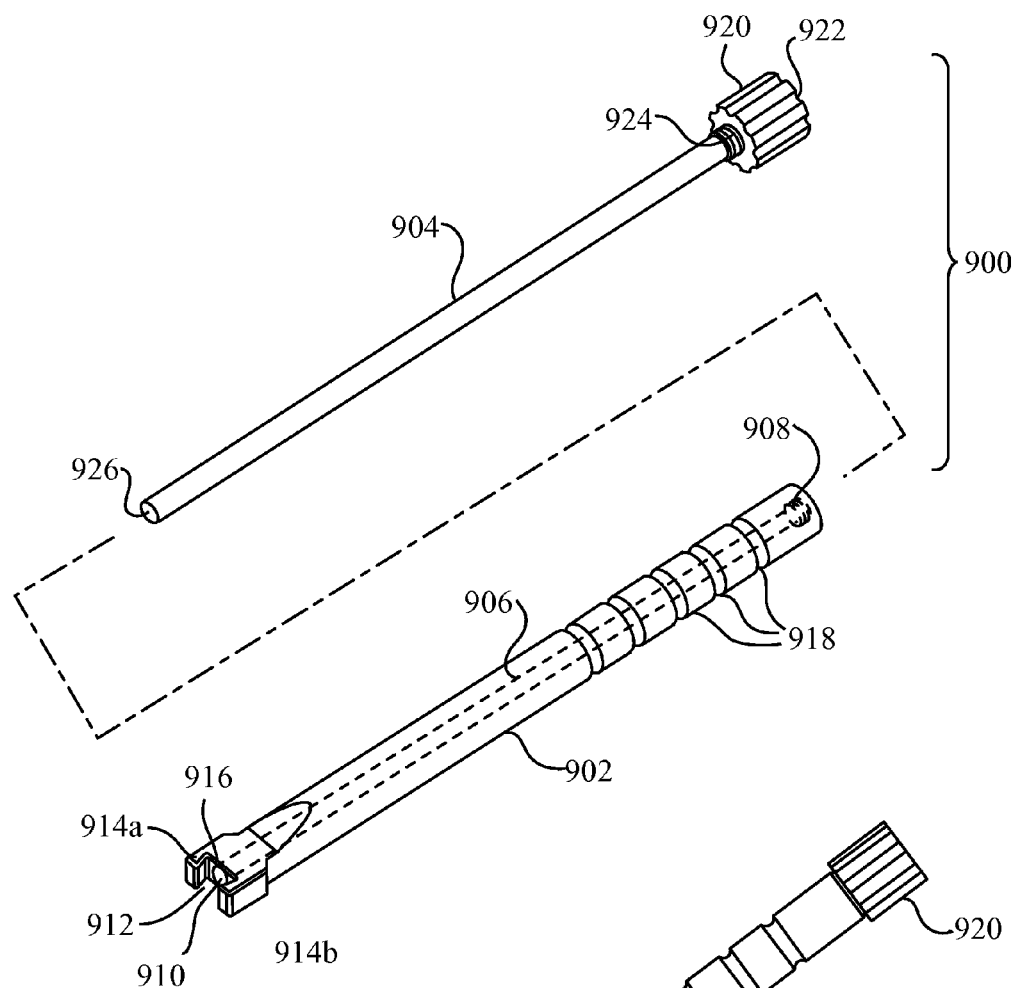
FIG. 27 is an assembly view of a tool for manipulating crimp lugs.
Figure 28:
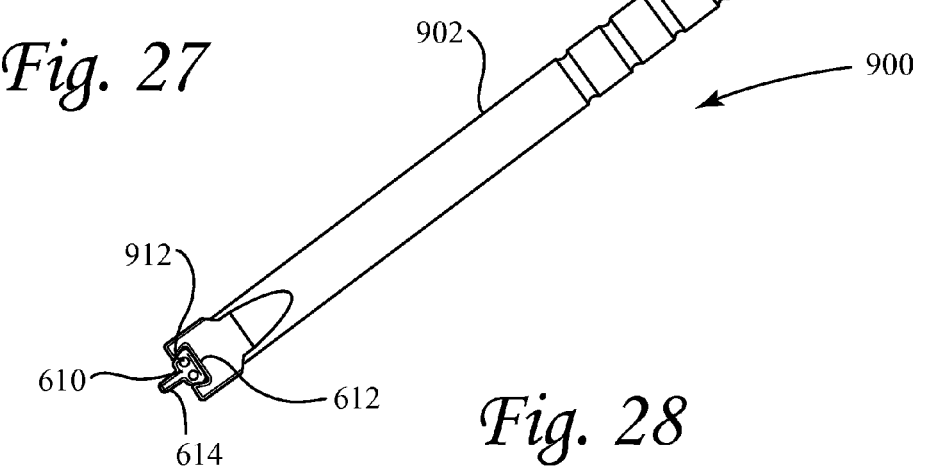
FIG. 28 is a perspective view of the tool of FIG. 27 provided with a crimp lug.

Referring to FIGS. 27 and 28, a tool 900 is provided for handling and inserting independent and discrete crimp lugs. The tool 900 includes a tubular housing 902 and a shaft 904 insertable within the housing. The housing 902 defines a central bore 906 having a thread 908 at its proximal end and opening 910 at a distal end to a lug receiver 912. The receiver 912 is defined by two arms 914*a*, 914*b* together with an end face 916 defining a trapezoidal opening sized to closely accommodate the trapezoidal head 612 of the lug 610, with the barbed tack 614 of the lug 610 extending distally from and beyond the receiver. It is appreciated that if the head of the lug is provided with another shape, the receiver is likewise designed to accommodate it in shape to closely receive it. The housing also preferably include external grooves 918 to facilitate secure manipulation. The shaft 904 includes a proximal end provided with knurled knob 920 having a preferably flat proximal end 922, threads 924 adjacent the knob, and a distal end 926. The shaft 904 is inserted into the bore 906 of the housing 902 and retained relative to the housing via engagement of the threads 924, 908. The housing 902 and shaft 904 can have a threaded engagement at alternative locations, such as about the exterior of the housing, or at or near the distal end of the tool.

In use, the knob 920 is rotated relative to the housing 902 to position the distal end 926 of the shaft in a retracted position relative to the distal opening 910. A crimp lug 610 is positioned in the receiver 912, and then the knob 920 is rotated to advance the distal tip in contact with the head 612 of the crimp lug 610 and secure it into the receiver 912. The lug 610 may then be easily manipulated by the tool 900. In addition, once the lug is maneuvered to the intended implant location, the proximal knob 920 of the tool may be struck with an impactor, such as a smaller hammer, to drive the lug 610 securely into bone. Then the knob 920 is rotated relative to the housing 902 to withdraw the distal tip 926 from contact against the head 612 of the lug 610 and release the lug from the tool 900.

Figure 20:
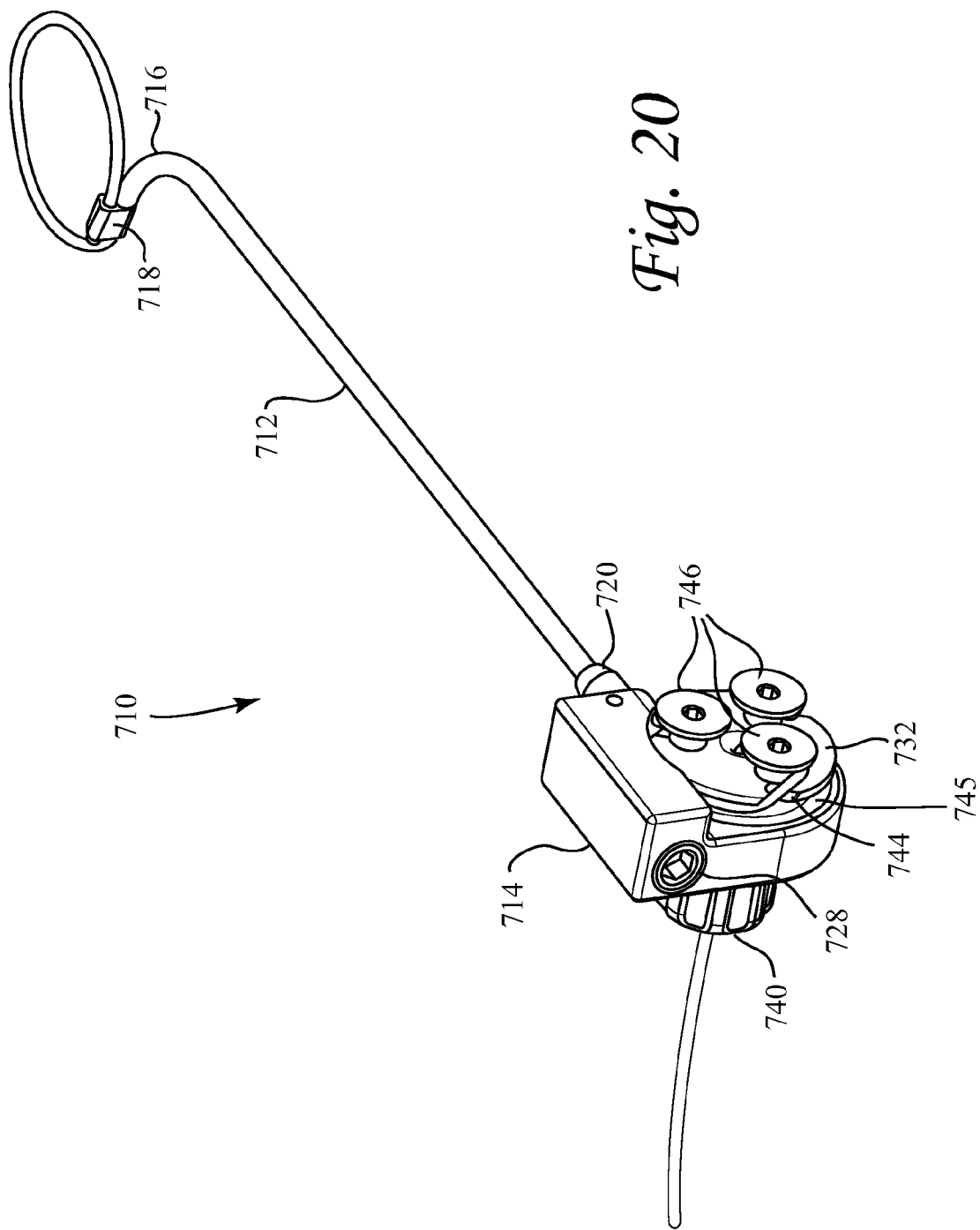
FIGS. 20 and 21 are proximal end perspective view of a cable tensioner.
Figure 21:
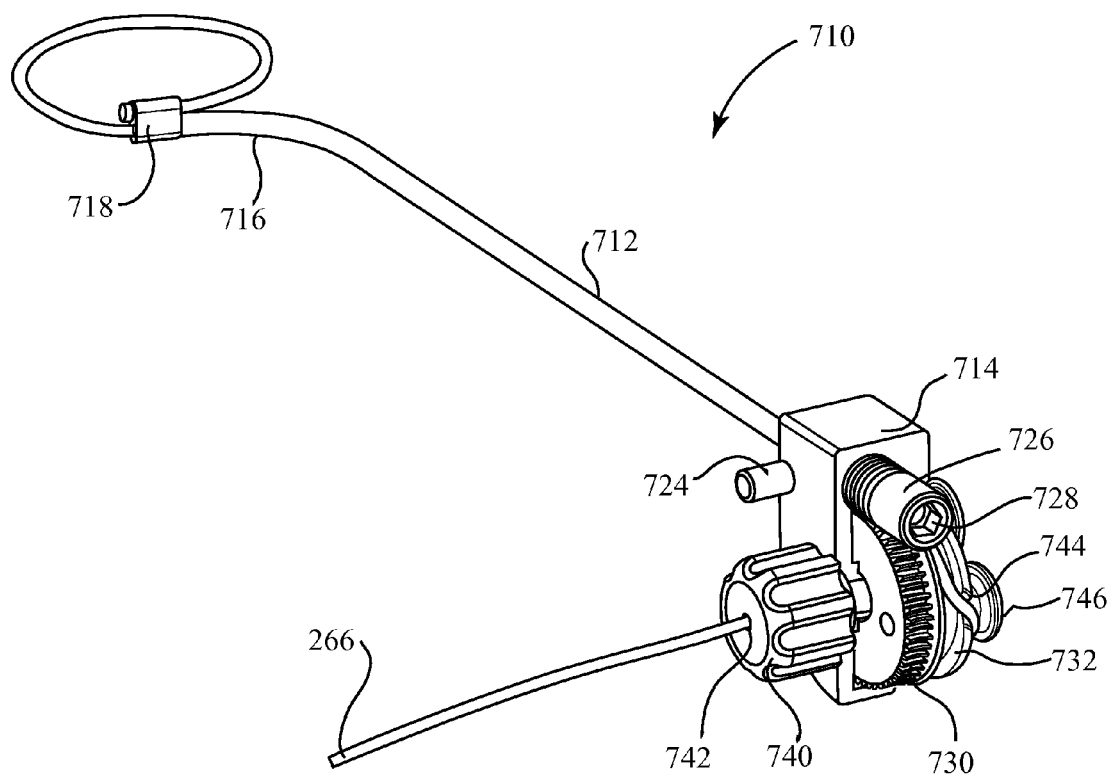
Figure 22:
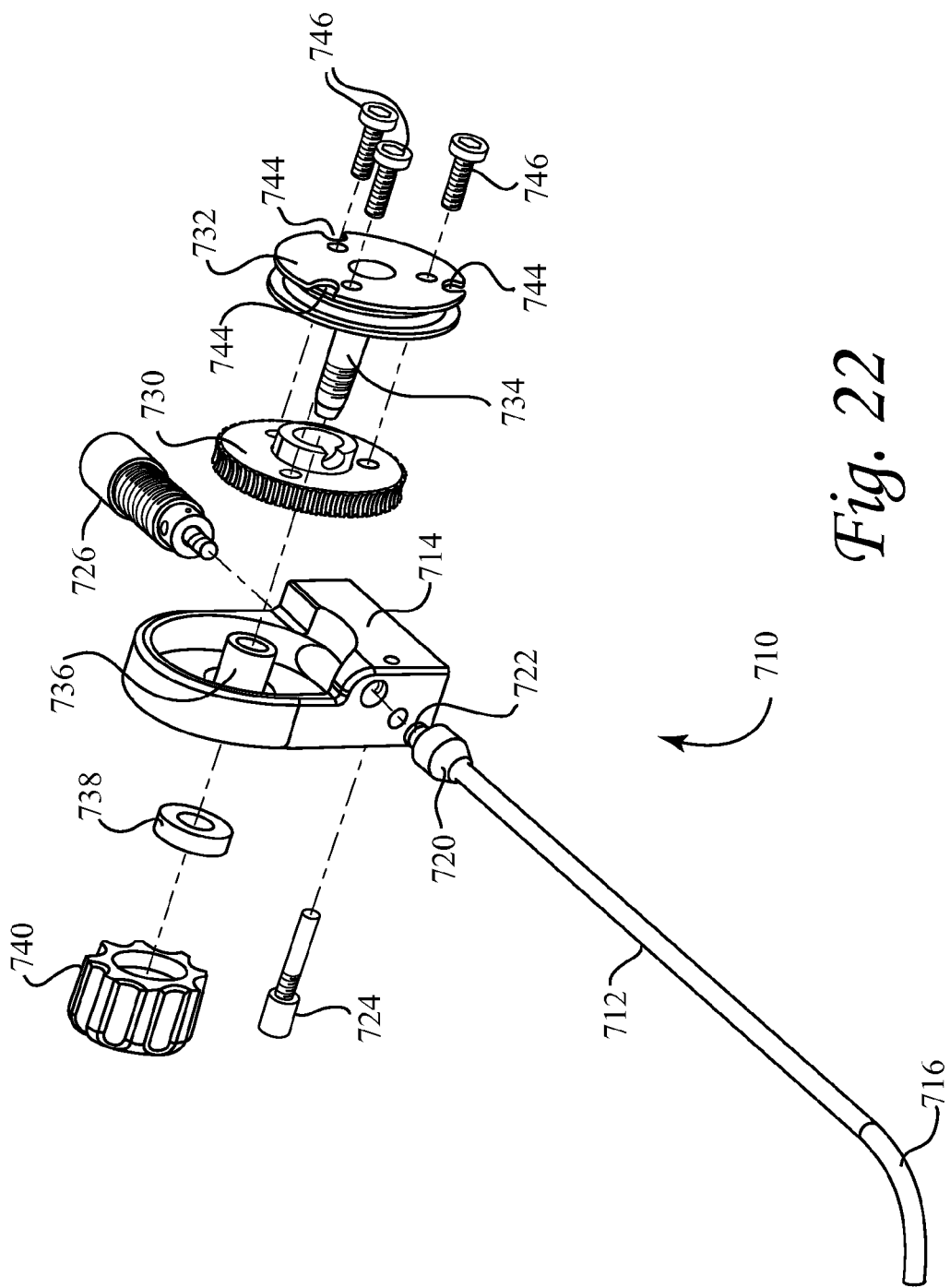
FIG. 22 is an assembly view of the cable tensioner of FIGS. 20 and 21.
Figure 23:
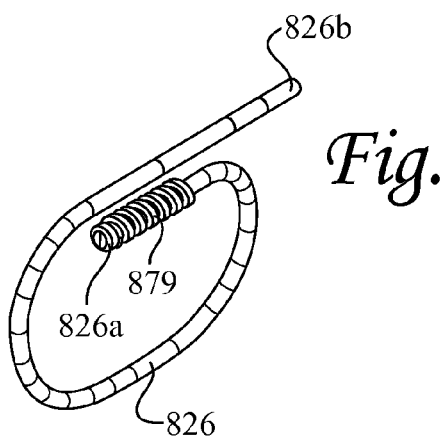
FIG. 23 is a perspective view of a wound cerclage cable provided with a spring according to an embodiment of the invention.
Figure 24:
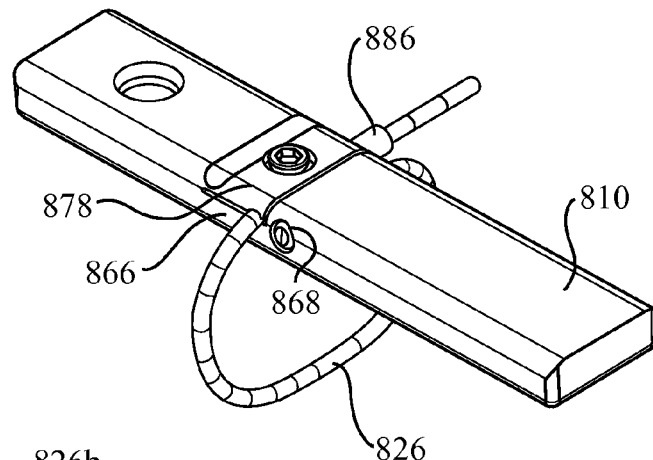
FIG. 24 is a perspective view illustrating the cerclage cable of FIG. 23 relative to an integrated cable retaining structure of a plate.
Figure 25:
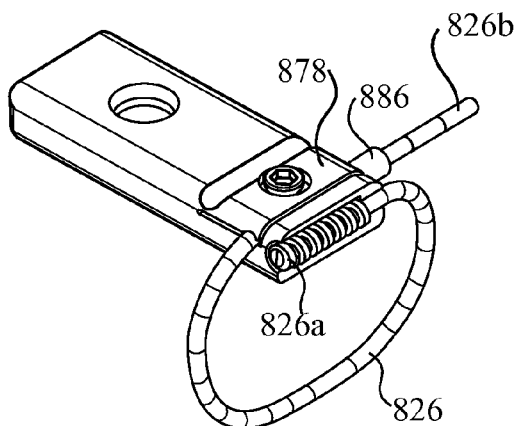
FIG. 25 is a view similar to FIG. 24 shown with a cross-section through second cable passage of the plate.
Figure 26:
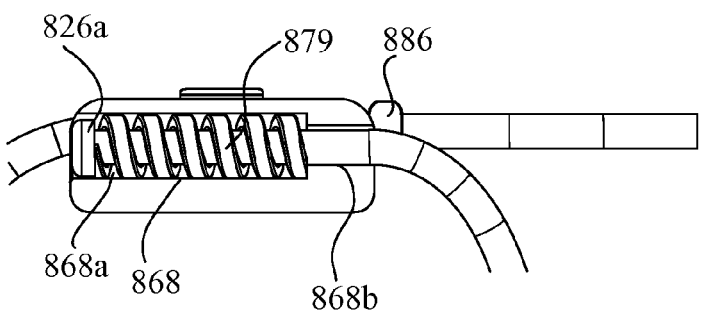
FIG. 26 is a side elevation view with a partial cross-section through the plate of FIGS. 24 and 25.

Turning now to FIG. 20 through 22, the system is also preferably provided with a cable tensioner 710. The cable tensioner 710 may be used to tension a cerclage cable advanced through the passages of an integrated cable securing structure on a plate, or through the eyelets of a separate crimp lug, or a simple crimp, each as described above, or in association with any plate or other cable securing component, whether or not having the foregoing features, but preferably having a passage through which a cable may be passed.

The cable tensioner 710 is a single device having a distal cerclage cable guide tube 712 leading to and connected to a proximal gear box housing 714. The tube 712 has a distal end 716 pre-formed with a gentle curve to facilitate the approach to a compression plate or cable lug 718 from outside a surgical wound. This provides the surgeon with additional space and clearance to work and displaces the working mechanism of the gearbox 714 away from the plate or crimp to retain visibility at the surgical site and working clearance. The proximal end 720 of the tube 712 is removably secured to the gearbox housing 714 with a lockpin 724 that engages a proximal lip 722 of the tube.

The gear box housing 714 includes worm screw 726 having a torque driver socket 728. The worm screw 726 is in gear-engagement to a drive gear 730 which is rotationally fixed to a cable pulley 732. A threaded tubular shaft 734 extends from the cable pulley 732 through a shaft mount 736 of the gear box housing 714. A collet 738 extends over the shaft 734. A locking knob 740 with a central opening 742 extends over the collet, and is threadedly mounted to the shaft 734 of the pulley 732. The tubular shaft 734, collet 738 and opening 742 define a cable passage extending transverse to the rotational axis of the worm screw 726. Rotation of the knob 740 in one direction decreases resistance to rotation of the pulley 732, whereas rotation of the knob in the opposite direction functions to increase resistance on pulley rotation relative to the housing 714. The pulley 732 has a plurality of grooves 744 opening in the sidewall of the track 745 of the pulley, and a guide bolt 746 or other guide structure located at each groove, the functions of each being described below.

In operation, after the free end of a cable 26b is advanced through a plate passage, lug 718, crimp, or other structure, with the stop end 26a of the cable retained in place, the free end 26b of the cable is then pulled and the distal end 716 of the tube of the cable tensioner is advanced towards the plate or crimp lug 718 until the tube 712 contacts or approximates the plate or crimp lug. The cable 26 may be threaded through the tube 712 with the tube separated from the gearbox housing 714, by removal of the lockpin 724. After the cable 26 has been advanced through the tube 712, the free end 26b is passed around the track 745 of the pulley 732 and through one groove 744 of the pulley 732 (generally the groove nearest the proximal end of the gear box, or furthest from the distal end of the tube), about the adjacent guide bolt 746, and through the cable passage defined by the tubular shaft 734, the collet 738, and the opening 742 in the locking knob 740. The pulley grooves 744 are preferably angled openings that will grab the cable 26 as the pulley 732 is rotated. The guide bolts 746 ensure a smooth transition by the cable 26 from the pulley 732 to a transverse orientation through the cable passage, without crimping or misfeed of the cable. If the tube 712 and housing 714 were previously disassembled (by removable of the lockpin 724), they are reassembled by inserting the lip 722 at the proximal end of the tube into the housing and re-inserting the lockpin 724 to engage the lip 722 and thereby prevent tube separation.

The cable 26 is then manually pulled until there is no cable slack between the tube 712 and the pulley 732. Then the locking knob 740 is rotated until a relatively taught cable 26 is secured in the proximal housing 714 of the tensioner 710, all without the need for a separate pretension clamp to hold tension on the cable. A driver (not shown) is next engaged in the socket end 728 of the worm screw 726. As the driver is rotated in a first direction the worm screw 726 rotates to "spool" the cable 26 about the pulley 732. The portion of the cable extending around the plate and bone decreases and compresses the plate onto the bone. Also, if the driver is rotated in an opposite second direction, the length of cable extending about the bone is increased, the tension on the cable is decreased, and the applied compression between the plate and bone is decreased. Rotationally driving the screw 726 provides superior tactile feedback over using a rotation knob or a pistol grip for applying tension on the cable and compression between the plate and bone. Once the desired compression is applied between the plate and bone, the integrated cable securing structure, crimp lug 718 or other structure is secured onto the cable 26 to retain the applied tension on the cable.

Figure 29:
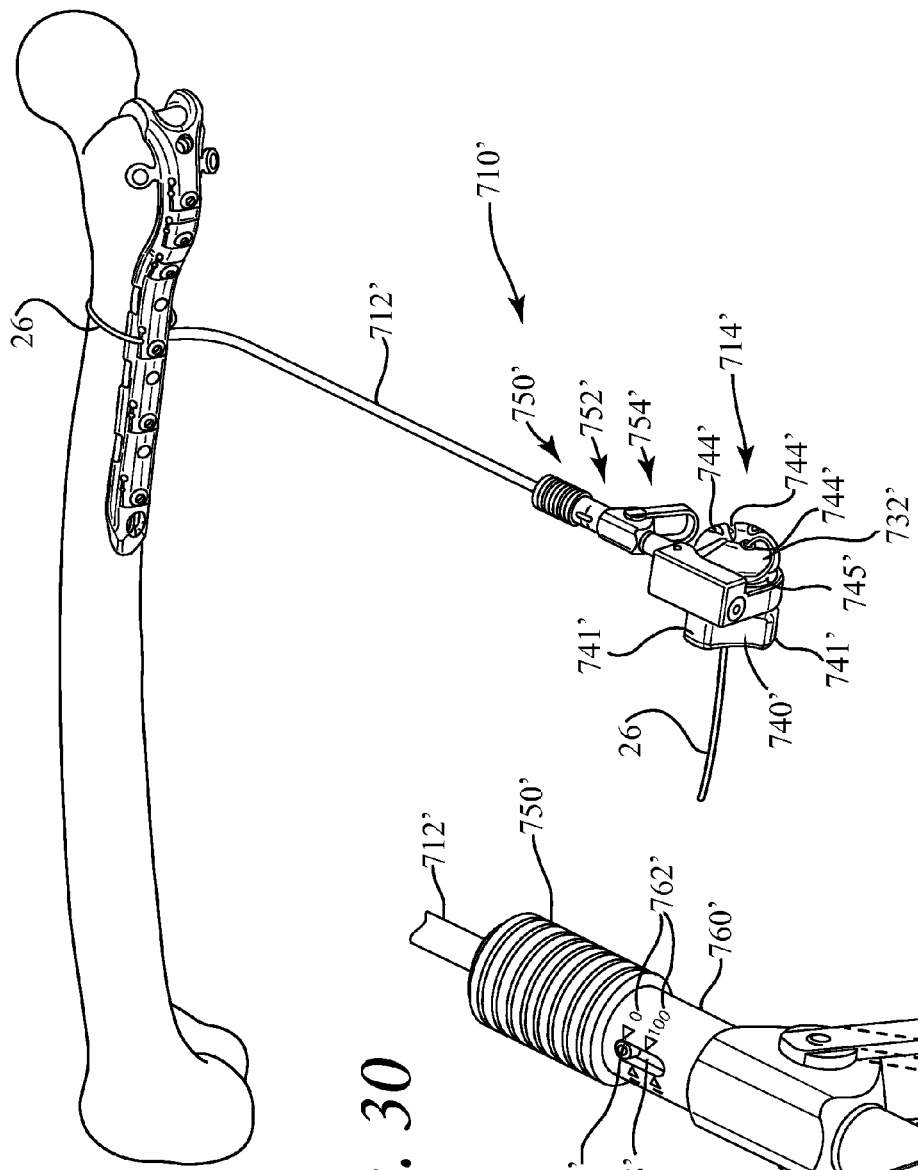
FIG. 29 is a perspective view of a cable tensioner shown applying a cerclage cable about a bone and plate.
Figure 30:
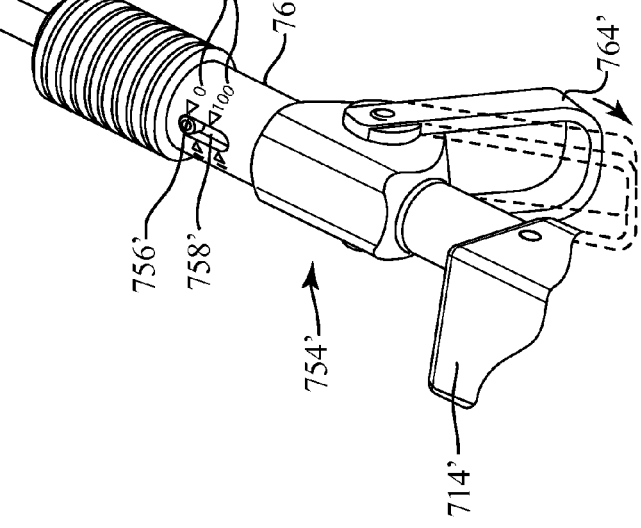
FIG. 30 is a broken enlarged portion of a tension gauge and cam lock of the cable tensioner of FIG. 29.
Figure 30A:
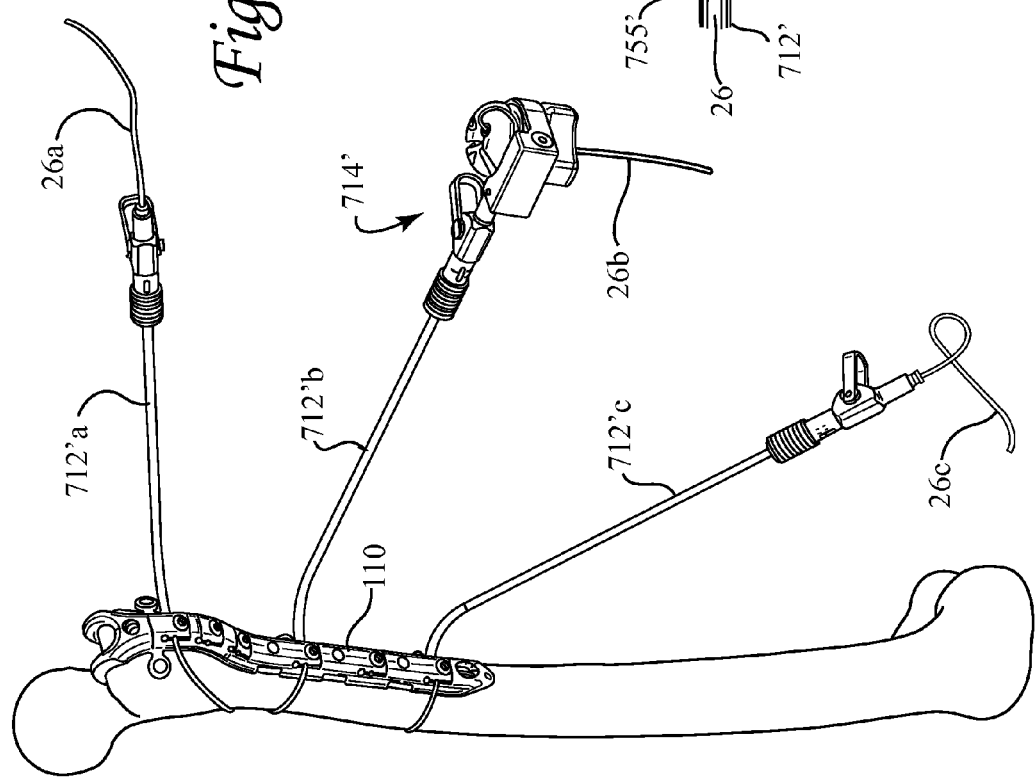
FIG. 30A is a longitudinal section view of the tension gauge and cam lock of the cable tensioner of FIG. 29.

Turning now to FIGS. 29 and 30, another embodiment of a cable tensioner 710', substantially similar to tensioner 710, is shown. The cable tensioner 710' has a guide tube 712' leading to and connected to a proximal gear box housing 714'. In distinction from the tensioner 710, the tensioner 710' includes several additional features that could similarly be incorporated into tensioner 710 or another tensioner. With additional reference to FIG. 30A, between the tube 712' and the housing 714', the tensioner 710' includes a compression spring 750', a tension gauge 752', and a cable tension lock 754'. The compression spring 750' is preferably a Belleville washer spring extending in outward compression. The gauge 752' includes a collar 753' having a shoulder 755' at the proximal end of the guide tube 712' that sits in contact with the distal end of the compression spring 750'. The gauge also includes a pin 756' that rides in a longitudinal slot 758' within a locking housing 760'. As tension is applied to the cable 26 by the gearbox in housing 714', the shoulder 755' is loaded against the spring 750' to compress the spring and thereby displace the pin 756' of the tension gauge 752' within the slot 758'. The pin 756' is displaced in proportion to the amount of force applied. Indicia 762' are provided along the side of the slot 758' to indicate the applied tension or relative tension. The cable tension lock 754' includes a cam arm 764' that rotates to move a cam 765' between a first position in which the cable can be longitudinally displaced relative to the tube 712', and a second position in which the internal cam 765' compresses against the cable 26 to lock its longitudinal position relative to the tube 712' (as shown in FIG. 30A). Other suitable locking mechanisms to temporarily fix the position of the cable and the tension thereon while the cable tensioner is in use can also be used.

Figure 29A:
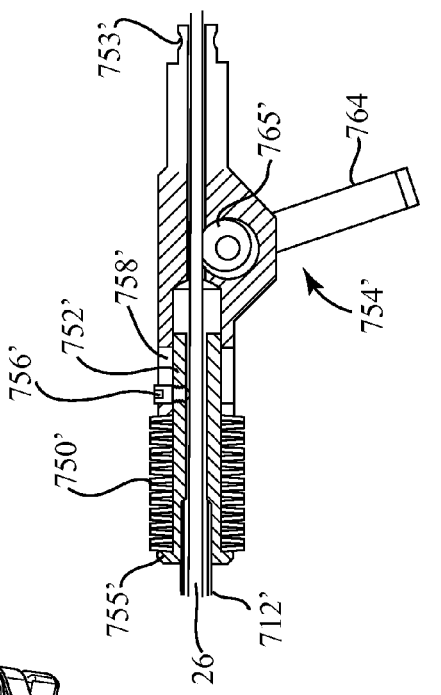
FIG. 29A is a perspective view of a cable tensioner shown applying multiple cerclage cables about a bone and plate.

According to another aspect of the invention, the gear box housing 714' can be disengaged and removed proximal to the cable tension lock 754', so that once the cable is tensioned and the lock is used to retain the tension, the housing can be removed to operate with another cable and tube and the tension on the cable is maintained. The housing can be removed from the relatively distal assembly by releasing lockpin 724' (see like component 724 in FIG. 21) or another retaining fastener which engages a grooved neck 753' at the proximal end of the tension lock 754' (FIG. 30A). As such, fewer components are required and costs can be reduced. More particularly, FIG. 29A illustrates a single gear box housing 714' being used sequentially with three tubes 712'a, 712b, 712'c, and cables 26a, 26b, 26c for preliminary application and maintenance of tension to the respective cables in advance of permanently fixing the tension on the cable with an appropriate plate 110 and/or lugs.

Turning back to FIG. 29, the gearbox housing 714' of the cable tensioner 710' is also provided with a pulley 732' and a locking knob 740', coupled to the gear box housing 714', each of a slightly different design than the respective counterparts in tensioner 710. Pulley 732' has a bulbous outer surface extending from the track 745' of the pulley, and three grooves 744' extending from the track over the bulbous surface into the cable passage (described above with respect to tensioner 710). Such design facilitates smooth guidance of the cable. The locking knob 740' is relatively larger than knob 740 and includes three large grips 741' (two shown) to facilitate handling and rotation of the knob 740'. The remaining components are substantially as described with respect to the gearbox of tensioner 710.

The cable tensioner 710, 710' is a single, small size, light weight instrument that can temporarily hold tension as well as increase tension to apply final securing tension. In addition, the device includes relatively few components and can be manufactured as either a reusable instrument, or as a one-time disposable instrument. The ease of use provides increased surgical efficacy and reduces the procedure time. Further, the device is relatively intuitive to use and can be learned without a significant learning curve.

It is recognized that certain periarticular fractures may not necessitate the use of a cerclage cable and the associated open surgical procedure necessary to implant such cable about the plate and the bone. If the option to avoid open surgery is available, it is often preferred, as trauma to the patient is reduced and recovery times can be significantly decreased. Various plates, such as mid-shaft plate 410 described above in association with FIG. 13 and a metaphyseal plate 1010 (1010a) described below in association FIGS. 31-39, are well-adapted for a minimally invasive 'closed' surgical approach in conjunction with a jig system, such as the jig system described below with respect to FIGS. 40-49.

Figure 31:
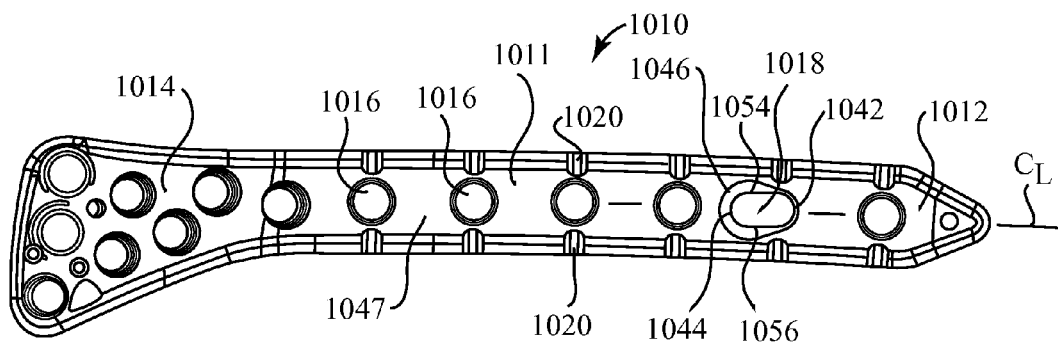
FIG. 31 is a top view of a distal femoral plate according to the invention.
Figure 32:
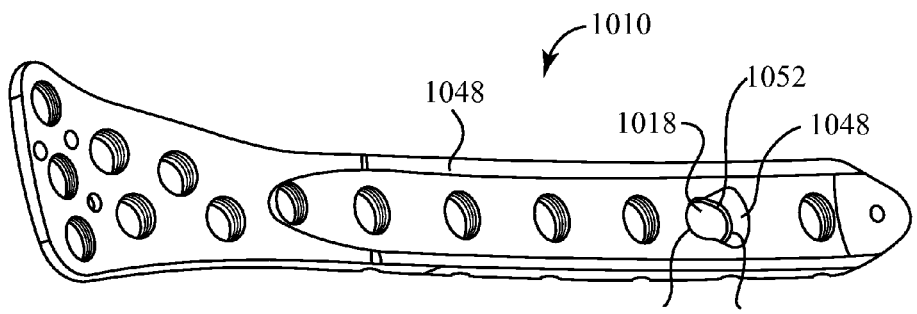
FIG. 32 is a bottom perspective view of the distal femoral plate of FIG. 31.
Figure 39:
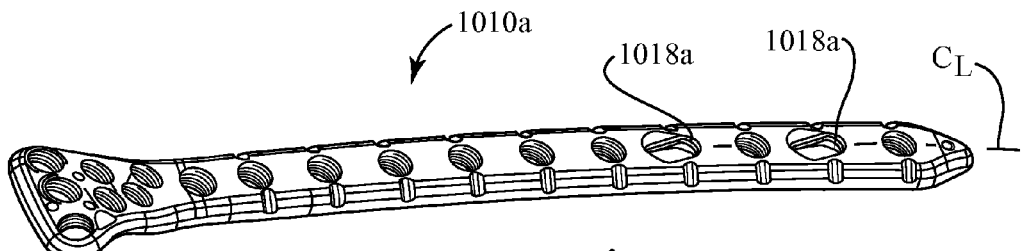
FIG. 39 is a top perspective view of another distal femoral plate illustrating an alternate arrangement of dynamic compression holes in the plate.

Turning now to FIGS. 31 and 32, a distal femoral plate 1010 is shown. The plate 1010 has a longitudinally extending shaft portion 1011 with a tapered proximal end 1012 to facilitate entry into a small incision and between the soft tissue and the bone. The distal end 1014 is shaped to accommodate the metaphysis of the distal femur. Alternatively, the distal end 1014 of the plate may include other structure than shown for placement against the metaphysis.

The plate 1010 includes screw holes 1016, 1018 at which bone screws can be selectively received, and optionally transverse grooves 1020 are provided adjacent such screw holes for the stabilized guidance of a cable (not shown) in the event the plate is utilized in an open procedure, to which the plate is also adapted. Grooves 1020 are described further with respect to FIG. 13. The screw holes include threaded holes 1016 that secure fixed angle bone screws (not shown) to the plate. Such fixed angle bone screw are known in the art and have a head with external threads that mate with the threaded holes to retain the screw directly to the plate 1010 and in alignment with a central axis of the threaded hole. Further, such fixed angle bone screws are adapted to not generate significant compressive force between the screw and plate as the screw is advanced into the bone and secured to the plate. The screw holes also include elongate, preferably non-threaded compression holes 1018, each for receiving a compression fastener 1024 (FIGS. 33-36) that utilizes the head 1026 of the screw to compress the bone plate 1010 against the bone 1030 as the threaded shaft 1028 of the screw is advanced into the bone. The head 1026 preferably has a convex lower surface 1032, which may alternatively be conical in design.

In accord with one aspect to the invention, the elongate compression holes 1018 are dynamic compression holes constructed to allow higher dynamic compression to be applied across a fracture beneath the plate than known compression holes permit. In general, dynamic compression holes are holes that are adapted to interact with a compression screw head to generate a longitudinal force on the screw, and thus against the bone into which the screw is driven. The force is a radial component generated by the shape of the screw head against one end of the compression slot. As the screw is axially driven, the underside of the head of the screw interferes with an end of the slot. As a result of the curvature (or angle) at the underside of its head, the screw head pushes radially outward from the end of the slot to result in displacement of the bone beneath the plate in a manner that effects compression across the fracture. In the prior art, as represented for example by U.S. Pat. No. 3,552,389 to Allgower et al., the amount of compression is constrained by the geometry of the screw. As a screw is driven, the bone displacement is limited to ½ (diameter of the screw head—major diameter of the screw shaft), which represents the radial overhang of a screw head beyond the screw shaft. In the dynamic compression holes 1018 of plate 1010, the displacement of the screw and the compression across the fracture is generated by the plate geometry and not necessarily the screw geometry. As a result, the magnitude of movement of the bone beneath the plate is not limited by the geometric constraints of the prior art.

More particularly, referring to FIGS. 31-33 and 37, the compression hole 1018 is an elongate hole that includes a screw ramp 1040 extending from a first end 1042 of the hole toward a second end 1044 of the hole, and a longitudinally flared recess 1046 adjacent the second end 1044 of the hole at the upper surface 1047 of the plate. In accord with another aspect of the invention, discussed below, the hole 1018 also includes a longitudinally flared lower recess 1048 beneath the first end 1042 of the hole, flaring in a direction opposite the upper recess 1046.

Figure 33:
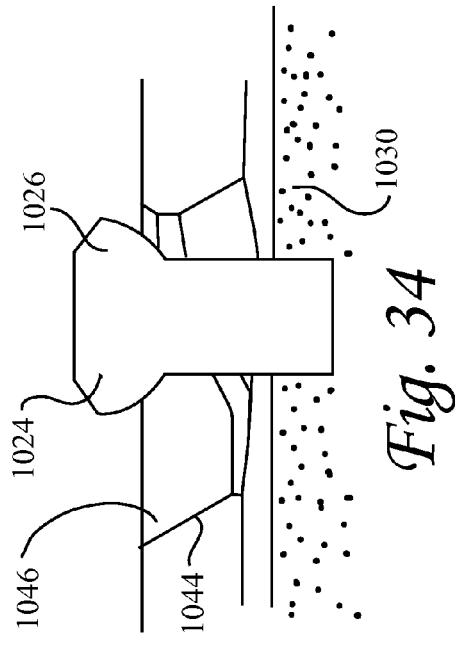
FIGS. 33 through 36 are schematic section views of a plate and bone screw illustrating the operation of a dynamic compression hole according to the invention.
Figure 36:
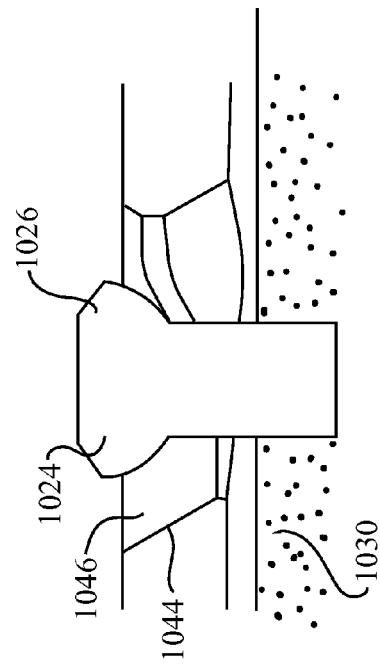
Figure 37:
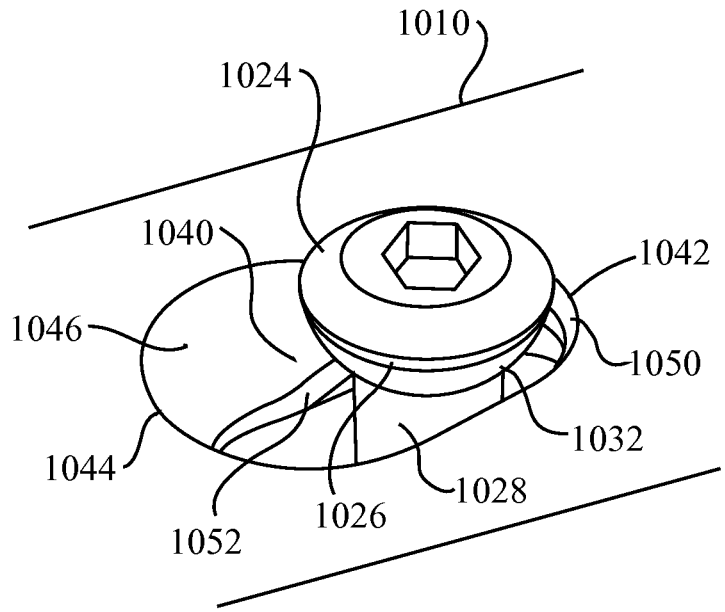
FIG. 37 is a schematic perspective view of a first position of a bone screw relative to a dynamic compression hole of a bone plate according to the invention.
Figure 38:
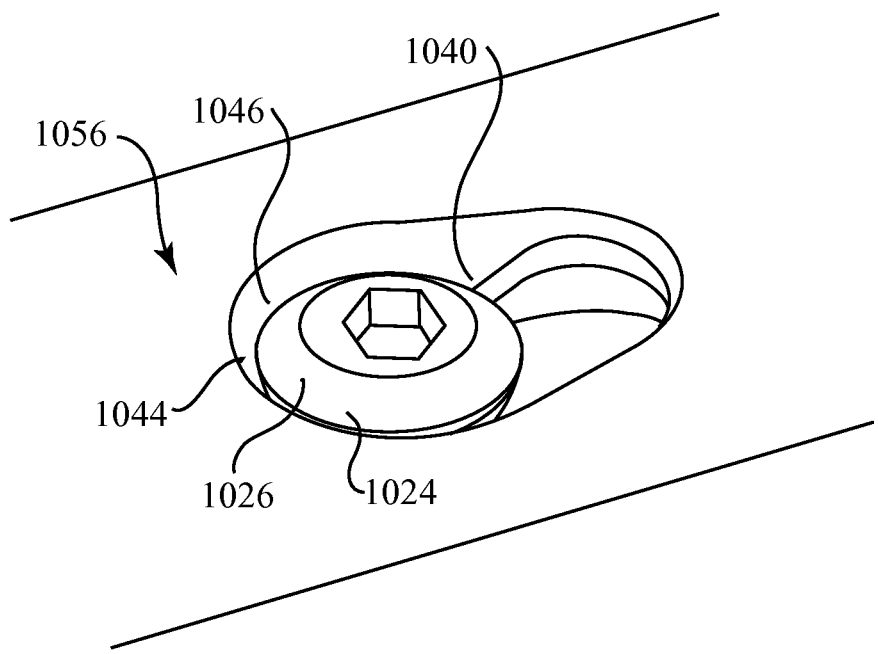
FIG. 38 is a schematic perspective view of a second position of a bone screw relative to a dynamic compression hole of a bone plate according to the invention.

In reference to when a lower bone contacting surface 1048 of the shaft of the plate 1010 extends along a substantially horizontal plane P (FIG. 33), the screw ramp 1040 has a downward slope, preferably at a constant angle, and has a length that extends preferably more than half the length of the screw hole 1018 and more specifically has a length sufficient to cause a screw head 1026 traveling down the ramp to contact the recess 1046 at the second end 1044 (i.e., far side) of the screw hole once the screw head has traversed to the bottom of the ramp, as shown through FIGS. 33-38. Referring to FIGS. 31, 33 and 37, the screw ramp 1040 includes an upper bevel surface 1050 against which the lower surface 1032 of the head 1026 of the screw contacts, and a side wall 1052 defining opposing sides 1054, 1056 with opposing points of contact which stabilize the shaft 1028 of the screw. In one embodiment, the opposing sides 1054, 1056 are straight and preferably vertical side walls. Alternatively, the opposing sides 1054, 1056 can have convex surfaces providing sufficient point contact relative to the shaft 1028 of the screw 1024 to stabilize the advancement of the screw through the hole.

Figure 34:
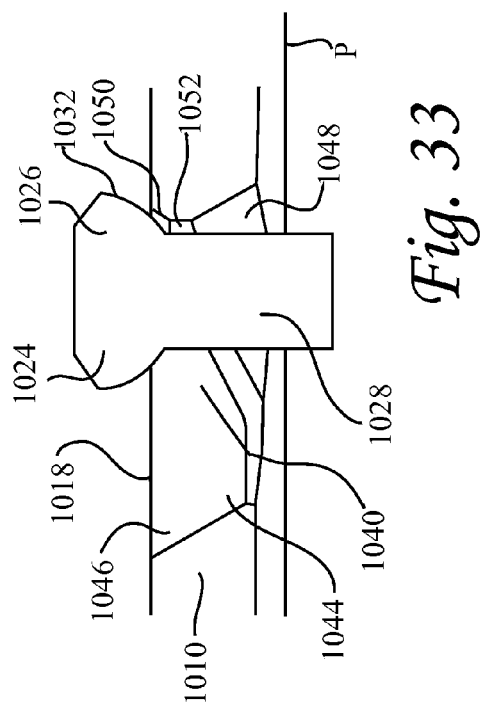
Figure 35:
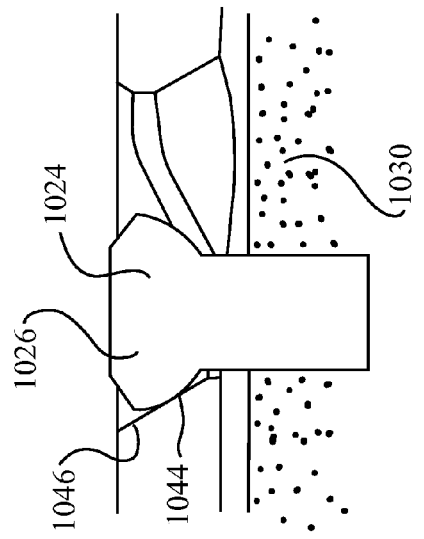

In operation, a first portion of the plate 1010 is longitudinally fixed to a bone with a first bone fastener on a first side of a fracture across which compression is required. Then, on an opposite side of the fracture, a screw 1024 is positioned with its shaft 1028 inserted adjacent the first end 1042 of the hole 1018. The screw 1024 is advanced into the bone until the lower surface 1032 of the screw head 1026 contacts the bevel surface 1050 at the first end 1042 (FIG. 33). Turning to FIGS. 34 and 37, as the screw 1024 is further advanced to provide compression against the plate 1010, the lower surface 1032 of the screw head will radially push off from the first end 1042, and the screw will seek to ride down the ramp 1040 to the lowest elevation within the screw hole. As the screw cannot longitudinally move within the hole as its is axially driven—the shaft is longitudinally fixed within the bone 1030—both the plate 1010 and the bone fixed to the plate at the first bone fastener move relative to the screw 1024. The screw is further advanced, as shown in FIGS. 34 through 36 and 38, drawing the fracture into compression until the screw head seats at the bottom of the ramp 1040 and in contact with the second end 1044 of the screw hole. The upper recess 1046 is adapted to accommodate the full size of the screw head 1026 so that the screw head seats flush or substantially flush with the upper surface 1056 of the shaft of the plate. Given the geometry of the screw hole, the potential displacement is limited only by the length of the ramp 1040. More specifically, it is anticipated that the compressive displacement will always be greater than the radial overhang of the screw head beyond the screw shaft, and more preferably at least twice the radial overhang, potential many multiples of the radial overhang. FIG. 36, by way of example only, illustrates a compressive displacement of approximately four times the radial overhang of the screw head beyond the screw shaft.

The direction of the compression hole is preferably perpendicular to the fracture line to provide maximum displacement of the plate relative to the fracture. The compression hole 1018 is shown extending parallel, and more specifically on axis with, the center line CL of the diaphyseal portion of the plate in FIG. 31. This arrangement accommodates the uncertainty of the location of the fracture line as well as a desirable aesthetic for the plate. As an alternative, referring to FIG. 39, plate 1010*a* is shown with the long axis of a compression hole 1018*a* obliquely oriented relative to the centerline of the plate to accommodate the curvature of the diaphysis of the bone and/or fracture locations and directionality shown to have an historical tendency to occur. By way of example only, the oblique orientation of the long axis may be at an angle between 0°-30° relative to the center line CL. Such hole orientation permits maximum compressive force to be applied perpendicular to a fracture line that is also oblique relative to the centerline of the plate. Further, plate 1010*a* illustrates that multiple compression holes 1018*a* can be provided along the shaft of the plate to provide options in the location at which compression is applied. For greatest mechanical advantage, it is most preferable to apply compression at the compression hole 1018*a* located closest to the fracture line; however given the uncertainty of the location of the fracture line, the plurality of compression holes along the shaft portion of the plate provides several options for most beneficial placement of the compression screw. Moreover, multiple dynamic compression holes in the same plate can have their axes obliquely and/or axially relative to the center line and extending at different sides relative to the center line to provide a best case approach for maximum compressive force perpendicular to a fracture line, particularly given the unpredictability of the fracture line.

Figure 40:
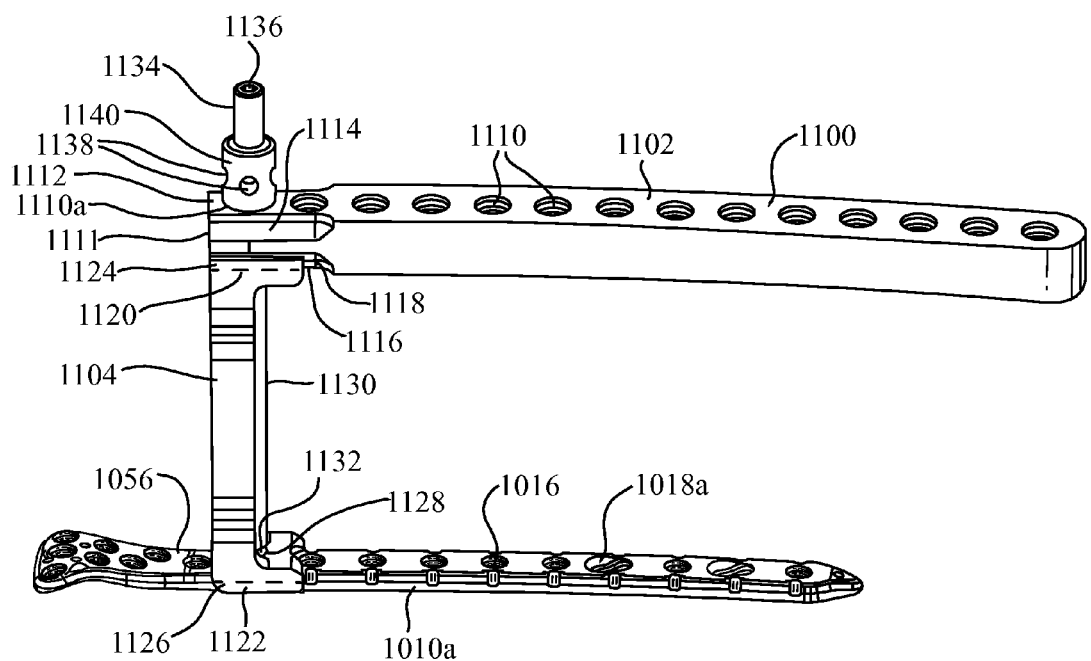
FIG. 40 is a perspective view of a screw implantation jig assembled to the plate of FIG. 39.

Turning now to FIG. 40, jig 1100 is shown coupled to the plate 1010*a* in a manner that facilitates minimally invasive insertion of the plate through an incision, and deploying screws from outside the patient, through the soft tissue surrounding the bone, and into the plate to secure the plate to the bone. The jig 1100 includes a jig arm 1102 that couples relative to the plate 1010*a* via a jig base 1104. The jig arm 1102 includes a plurality of jig holes 1110 having the same center-to-center spacing as the screw holes 1016 of the bone plate, and being configured to orient components inserted therethrough over the screw holes 1016, 1018*a* of the plate, as described below. All of the jig holes 1110, with the exception of the one jig hole 1110*a* located nearest a first end 1111 of the jig arm, are threaded. The jig arm 1102 may be straight or curved as necessary to extend over the plate 1010*a*, and is preferably designed with a sufficient number of jig holes 1110 to separately accommodate plates of various lengths, provided such various length plates each have holes that are arranged along a common longitudinal axis, extend in common axial orientation, and have a common inter-hole spacing. Alternatively, separate jig arms may be provided for plates of individual sizes and curvatures. The first end 1111 of the jig arm includes a first side 1112 with a reduced stepped width first portion 1114, and a second side 1116 with a stepped reduced width second portion 1118. The jig holes 1110 extend between the first and second sides 1112, 1116. The jig base 1104 includes first and second ends 1120, 1122, each provided with a respective recess 1124, 1126, and a throughbore 1128 extending in communication between the first and second recesses 1124, 1126.

In assembling the jig 1100 to the plate 1010*a*, the jig base 1104 is positioned over a threaded screw hole 1016 on the plate, with the base 1104 straddling the upper surface 1032 of the plate 1010*a* at the second recess 1126. The jig arm 1102 is adapted such that either of the reduced width first or second portions 1114, 1118 can be received in the upward oriented first recess 1124. The orientation of the jig arm 1102 is generally dependent on whether the plate is adapted for a left or right side bone of the patient and the adaptive contours of such plate; the jig arm 1102 is always oriented within the first recess 1124 to follow any curvature of the underlying plate 1010*a*.

A locking guide 1130 is then inserted through the jig hole 1110*a* at the first end 1111 of the arm, through the throughbore 1128, and into an underlying threaded screw hole 1016 of the plate 1010*a*. Referring to FIG. 42, the locking guide has a longitudinal bore 1150. The distal end of the locking guide 1130 has a tapered threaded portion 1132 and is split at two orthogonally oriented compression slots 1140, 1142 extending longitudinally into the distal end of the guide 1130. The tapered threaded portion 1132 is adapted to threadedly engage threaded screw holes 1016. The tapered and split construction allows the guide to be rapidly advanced into the screw holes 1016, yet allows significant radial loads to be developed at the threads as the tapered threaded portion 1132 is advanced into a threaded hole 1016 to provide a secure engagement at the plate 1010*a*. Turning back to FIG. 40, a proximal end 1134 of the locking guide preferably includes an axial driver recess 1136, such as a hex opening to drive the guide 1130 relative to the jig 1100 and plate 1010*a*. In addition or alternatively, radial through-holes 1138 in which to receive a lever to apply torque to the locking guide are radially displaced, preferably at 90° apart, about the proximal end of the locking guide. Such through-holes 1138 can be located on a larger diameter collar 1140 fixed at the proximal end of the guide to provide increased mechanical advantage. In addition or alternatively, external flats, such as in the form of a hex, can be formed on the outer proximal end of the locking guide, including the collar 1140, to facilitate engagement by a tool to apply torque.

Once the jig 1100 is rigidly assembled relative to the plate 1010*a*, the jig can be used as a handle to manipulate the plate, and advance the tapered end 1012 of the plate through a small incision until the plate lies in an intended position between long bone and the overlying soft tissue. By way of example, the long bone is the femur and the soft tissue is muscle, facia, and skin surrounding the femur. The plate is then fixed relative to the bone with screws. If the plate includes a portion having bone screw holes which are exposed at the incision such as metaphyseal portion 1014 of the plate 1010*a*, such portion is preferably first coupled to the bone to provide initial plate fixation.

Figure 41:
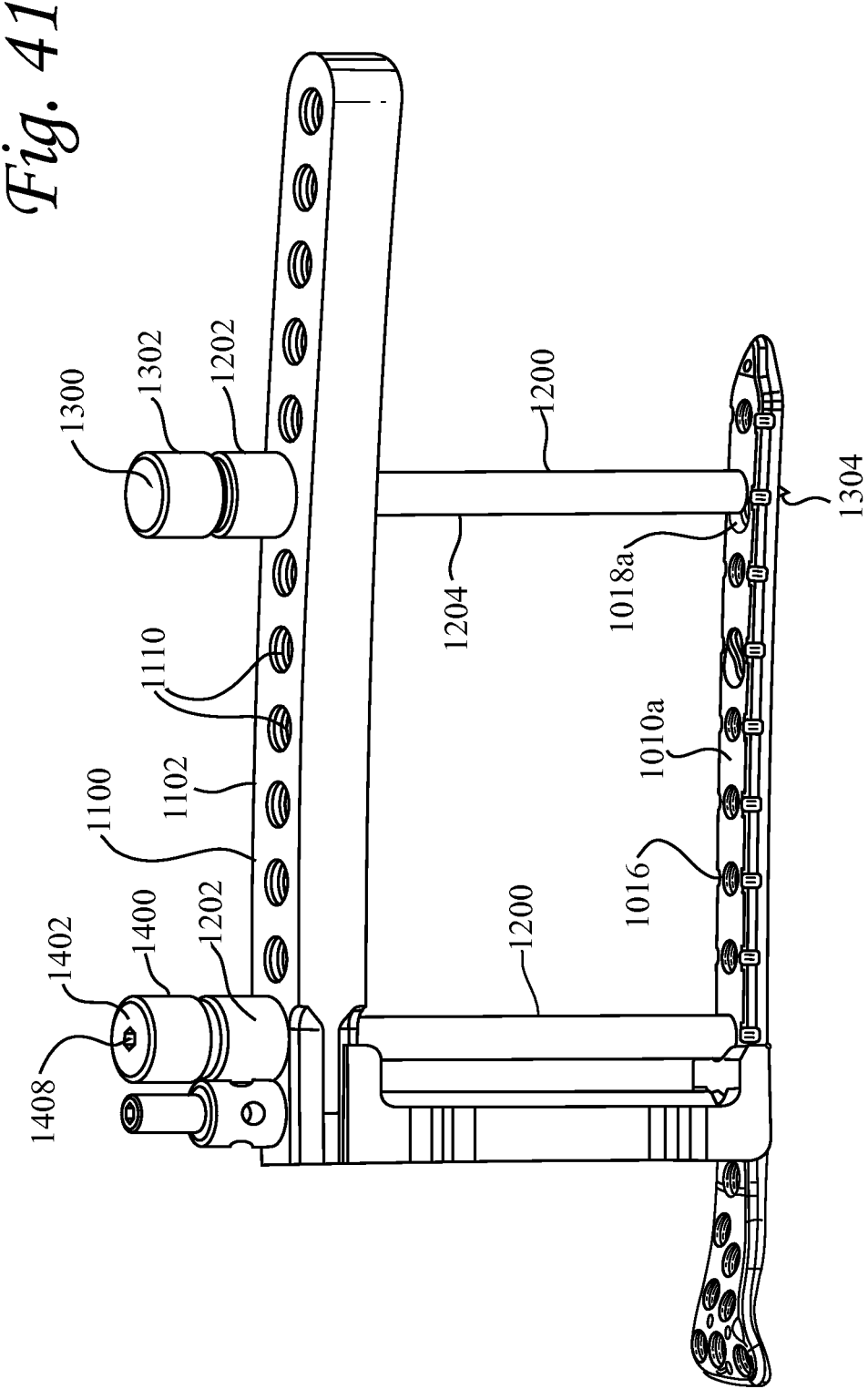
FIG. 41 is a perspective view of the screw implantation jig assembled to the plate and with tissue penetration and drill guide tools coupled to the jig and plate.

Then, each bone screw used for securing the plate at portions remaining unexposed beneath the soft tissue is advance through the soft tissue and to the plate preferably in accord with the following method, generally illustrated in FIG. 41. However, it is noted that FIG. 41 illustrates various stages of the methodology, which would not necessarily be occurring at the same time during a surgical procedure. As such, FIG. 41 should be considered as illustrative only and should be considered in context of the following preferred order for steps for the procedure.

Referring to the right side of FIG. 41, a trocar 1300 is slidably disposed within an outer sleeve 1200, and the two are together advanced through the soft tissue down to the plate 1010*a*. The outer sleeve 1200 has a proximal collar 1202 and a sleeve 1204 with a length adapted to extend from the first side 1112 of the jig arm to the upper surface 1032 of the plate 1010*a*. As shown in FIG. 43, a proximal end 1206 of the sleeve is provided with external threads 1208 adapted to threadedly engage the jig holes 1110 to fixedly couple the outer sleeve 1200 relative to the jig 1100, and consequently the plate 1010*a*. The trocar 1300 has a proximal collar 1302 adapted to rest on the collar 1202 of the outer sleeve 1200, and a pointed distal end 1304 adapted to penetrate and separate the soft tissue as the two are advanced. The trocar 1300 has a length such that once the sleeve 1200 is fixedly coupled to the jig arm 1102, the trocar 1300 can extend completely through the soft tissue, through the respective screw hole, and provide an initial pilot marking on bone when the collars 1202, 1302 are in an abutting relationship. The trocar 1300 is then removed, while the outer sleeve 1200 remains fixed in place.

Figure 46:
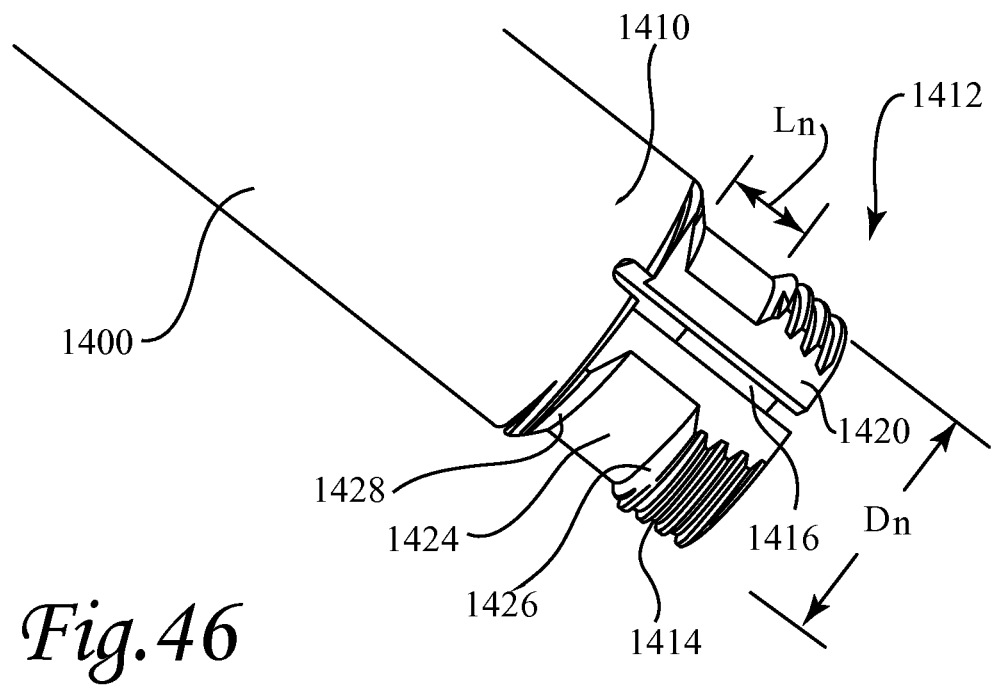
FIG. 46 is a perspective view of a distal end of the drill guide of FIG. 44.
Figure 47:
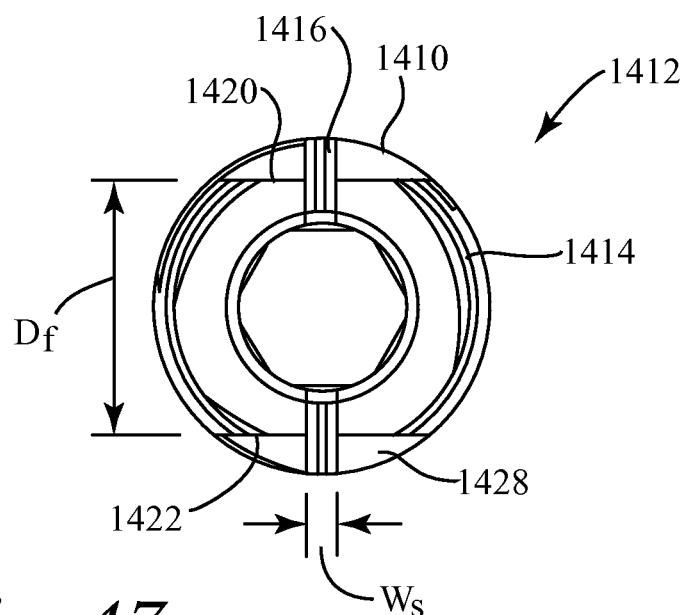
FIG. 47 is a distal end view of the distal end of the drill guide of FIG. 44.
Figure 48:
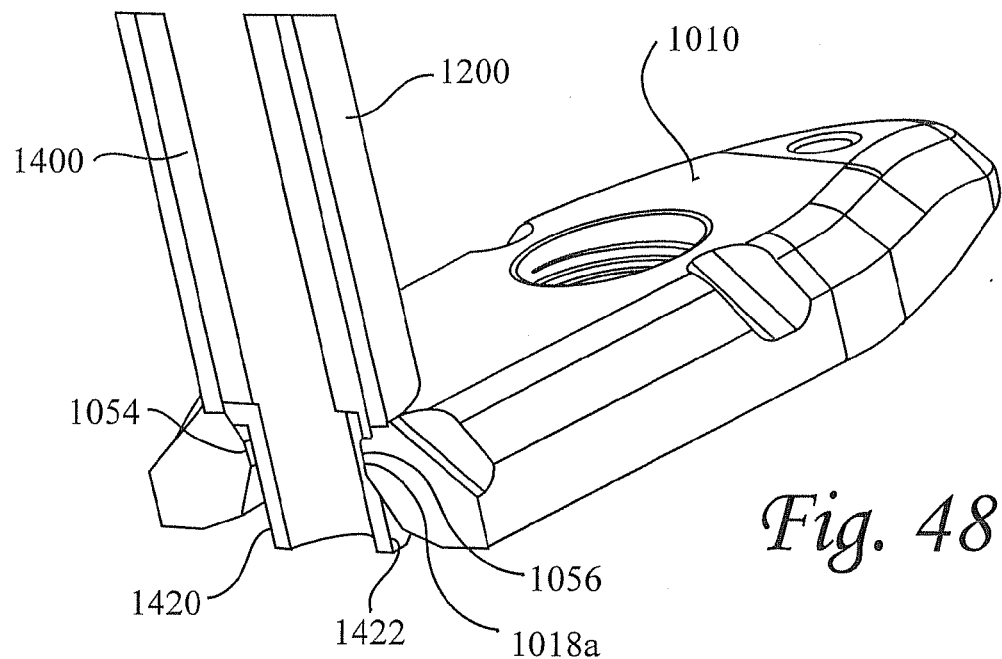
FIG. 48 is a broken section view of the outer sleeve positioned adjacent the upper surface of the plate, and the drill guide in a first rotational orientation extended through a dynamic compression hole.

Referring to the left side of FIG. 41, an outer sleeve 1200, advanced with a trocar 1300 as described above, is shown in place adjacent the locking guide 1130. After the trocar 1300 is removed, a drill guide 1400 is advanced through the outer sleeve 1200. As shown in FIGS. 41, 44 and 45, the drill guide 1400 includes a proximal collar 1402 and a tubular member 1404 with a longitudinal bore 1406. The collar 1402 is sized to stably seat on the collar 1202 of the outer sleeve 1200 and functions as a manual handle for manipulating the guide 1400. Optionally, an axial driver recess 1408 for coupling a torque driver to the collar 1402 is provided its proximal end. It is appreciated that the collar 1402 is sized to be used as a handle for manual rotation as well. In accord with one aspect of the invention, the tubular member 1404 has a distal end 1410 provided with hole engagement structure 1412 adapted to couple with either a threaded hole 1016 or a non-threaded slot 1018*a* in the bone plate 1010*a*. Turning now to FIGS. 46 and 47, the hole engagement structure 1412 includes a tapered threaded portion 1414 threadedly engagable with the threaded screw hole 1016. A neck portion 1424 is provided proximally to the threaded portion 1414. The neck portion 1424 has a reduced diameter relative to the threaded portion 1414, a maximum diameter Dn greater than the width of the screw hole slot 1018*a*, and a length Ln exceeding the thickness of the sides 1054, 1056 of the screw hole slot 1018*a* (FIG. 48). A lip 1426 is defined at the upper end of the threaded portion 1414, and a shoulder 1428 is defined at the proximal end of the neck portion. The hole engagement structure 1412 also includes opposing flats 1420, 1422 extending longitudinally through the threaded portion 1414, the lip 1426, and the neck portion 1424. The flats 1420, 1422 are displaced apart from each other by a distance Df which is less than the width of the screw hole slot 1018*a* at the sides 1036, 1038. A compression slot 1416 extends diametrically and longitudinally through an entirety of the flats 1420, 1422, and further in a direction transverse to the maximum diameter Dn of the neck portion. While the diameter Dn is greater than the width of the screw hole, it does not exceed the width of the screw hole slot 1018*a*, as defined as the dimension between the sides 1036, 1038, by more than the width Ws of the compression slot 1416.

Where the drill guide 1400 is advanced through the outer sleeve 1200 and into position over a threaded screw hole 1016 of the plate 1010*a* (as shown with respect to the position of the left outer sleeve 1200 in FIG. 41), the drill guide is threadedly engaged with the threaded screw hole at the threaded portion 1414. A torque driver (not shown) may be coupled to the drill guide 1400 at the recess 1408 to apply sufficient torque to the drill guide in order to secure the assembly of the guide 1400 to the plate 1010*a*. As the torque is increased, the distal end of the guide may compress across the compression slot 1416 increasing the resistance to unintended pullout. Once the drill guide 1400 is securely engaged to the plate, a drill bit is advanced through the drill guide and operated to drill a hole for the shaft of the bone screw at the location beneath the bone plate. The drill is removed, and then the drill guide 1400 is removed. A fixed angle screw is advanced through the outer sleeve 1200 and driven into the bone and plate 1010*a* with a torque driver. The outer sleeve 1200 is then removed from engagement with the jig 1100.

Figure 49:
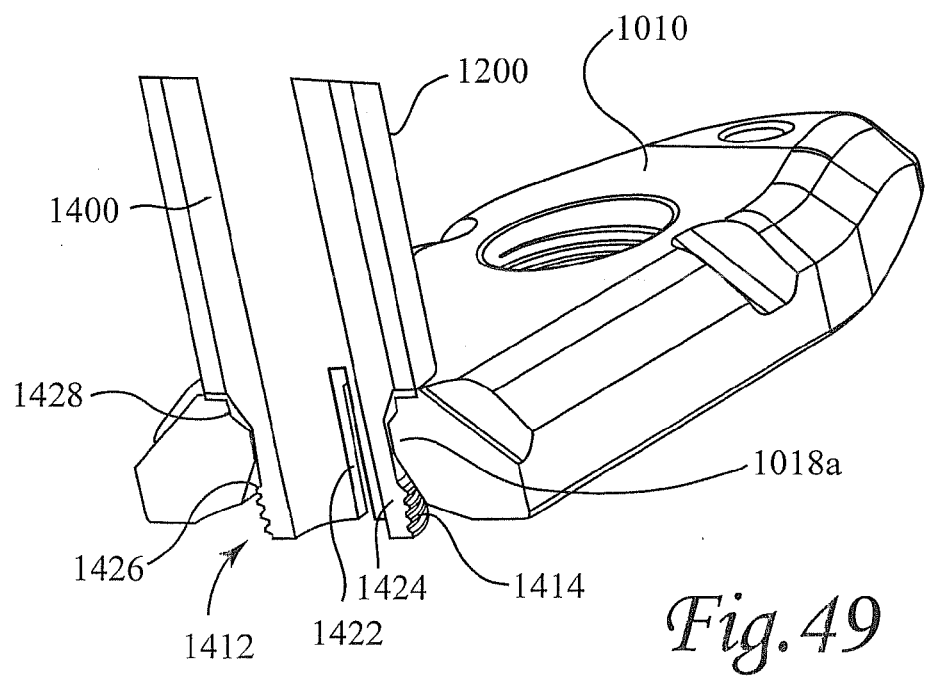
FIG. 49 is a broken section view of the outer sleeve positioned adjacent the upper surface of the plate, and the drill guide in a second rotational orientation locked relative to the plate at the dynamic compression hole.

Referring to FIGS. 48 and 49, where the drill guide 1400 is advanced through the outer sleeve 1200 and into position over a non-threaded elongate dynamic compression slot 1018*a* (as shown with respect to the position of the right outer sleeve 1200 in FIG. 41; i.e., with the drill guide replacing the position of the trocar 1300 shown in FIG. 41), the drill guide is rotated such that the flats 1420, 1422 are parallel to the elongate sides 1054, 1056 of the slot 1018*a*. In this orientation, the threads 1414 are passed through the screw slot 1018a, without threaded engagement thereof, and until the neck portion 1424 resides within the screw slot. The drill guide 1400 is then rotated one quarter turn; i.e., by 90°, in either rotational direction about its longitudinal axis. As the diameter Dn of the neck portion 1424 is greater than the width of the screw hole slot 1018a, but not by more than the width Ws of the compression slot 1416, the neck portion 1424 radially compresses like a spring about the compression slot 1416. (See FIGS. 46-47 regarding the referenced dimensions.) This results in the hole engagement structure 1412 capturing the plate at the compressed neck portion 1424 and between the lip 1426 and the shoulder 1428, thereby locking the dill guide 1400 relative to the hole 1018a. The lower recess 1048 surrounding the first end 1042 of the compression screw hole 1018a (shown in FIG. 32) provides clearance for rotation of the lip 1426 into the locking position. The surgeon receives tactile feedback as the compression increases, and is thus provided feedback as to the secured relationship of the guide 1400 relative to the plate 1010a.

Once the drill guide 1400 is securely engaged to the plate, a drill bit is advanced through the drill guide and operated to a drill hole for the shaft of the bone screw at the location beneath the bone plate. The drill is removed, and then the drill guide is removed. A compression screw is advanced through the outer sleeve 1200 and driven into the bone and plate 1010a with a torque driver. It may be necessary to loosen the outer sleeve relative to the jig arm to fully seat the screw, as the screw head may slightly longitudinally displace due to seating in a dynamic compression holes; however, the sleeve should remain within the soft tissue to protect the soft tissue from the torque driver. Once the screw is seated, and the torque driver removed, the outer sleeve is removed from engagement with the jig arm 1102.

The above steps are repeated as necessary for each threaded screw hole and compression screw hole receiving a bone screw. Finally, referring back to FIGS. 40 and 42, a hole is drilled through the bore 1150 of the locking guide 1130, and then the locking guide is unscrewed from the jig 1100 so that the jig is disassembled from the plate 1010a. The outer sleeve 1200 is advanced into the position formerly occupied by the locking guide 1130, and a bone screw is advanced to the plate 1010a and driven into the plate and bone to complete the implantation.

There have been described and illustrated herein embodiments of a system, devices, and methods relating to periprosthetic fracture fixation. While particular embodiments of the invention have been described, it is not intended that the invention be limited thereto, as it is intended that the invention be as broad in scope as the art will allow and that the specification be read likewise. Thus, it is specifically intended that various features described with respect to different embodiments of the compression plates, cable securing structure, and crimp lugs be usable interchangeably in other plates, and specifically in plates combining a plurality of the described features, as such structure permits. Further, while the plates and systems have been specifically described with respect to fixation and stabilization at the femur, it is appreciated that such plates or like plates of suitable size and shape can be adapted for periarticular fixation of other long bones. Moreover, while the features herein have been described in the context of periarticular fixation, it is appreciated that the structure and use is not limited thereto, and may have additional utility particularly in other areas of orthopedic fixation, other surgical procedures, and even non-medical applications. It will therefore be appreciated by those skilled in the art that yet other modifications could be made to the provided invention without deviating from its spirit and scope as claimed.

What is claimed is:

1. A cable tensioner for applying tension to a cable relative to a plate or cable securing structure, said cable tensioner comprising:
   a) a tube having a proximal end and a distal end;
   b) a gearbox coupled to said proximal end of said tube, said gearbox including, a worm screw, a drive gear in engagement with said worm screw, and a cable pulley rotationally fixed to said drive gear and rotatable about a pulley axis, said cable pulley including structure to engage the cable, a cable passage being defined transverse to said pulley axis, wherein when the cable is placed through said tube, over said pulley, and through said cable passage, and said tube is advanced over the cable such that said distal end of said tube is contacted against the plate or the cable securing structure with which the cable is used, rotation of said drive gear operates to pull the cable into tension; and
   c) a cable tension lock removably engaged to the gearbox, the cable tension lock configured to lock and unlock an applied tension on the cable, wherein said gearbox is removable relative to said cable tension lock while said cable tension lock holds an applied tension on the cable.

2. A cable tensioner according to claim 1, further comprising:
   a knob coupled relative to said pulley, wherein rotation of said knob in one direction operates to increase resistance on said pulley, and rotation of said knob in an opposite second direction operates to decrease resistance on said pulley.

3. A cable tensioner according to claim 2, wherein:
   said cable passage is defined through said drive gear, said pulley and said knob.

4. A cable tensioner according to claim 3, wherein:
   said cable pulley has a tubular shaft at least partially defining said cable passage.

5. A cable tensioner according to claim 2, wherein:
   said knob and said pulley are located on opposite sides of said drive gear.

6. A cable tensioner according to claim 2, wherein:
   said knob and said pulley are located on opposite sides of said worm screw.

7. A cable tensioner according to claim 1, wherein:
   said worm screw has a proximal torque driver socket.

8. A cable tensioner according to claim 1, wherein:
   said pulley defines a circumferential cable track having a sidewall, and said structure to engage the cable includes at least one groove opening in said sidewall of said track.

9. A cable tensioner according to claim 8, wherein:
   said pulley includes a guide structure located at said groove for guiding the cable from said groove of said cable track into said cable passage.

10. A cable tensioner according to claim 1, wherein:
    said distal end of said tube is curved.

11. A cable tensioner according to claim 1, wherein:
    said proximal end of said tube is releasable from said gearbox.

12. A cable tensioner according to claim 1, in association with:
    a flexible inelastic cerclage cable having a first end provided with a stop and a second end, said cable extending through said tube, about a portion of said pulley and through said cable passage.

13. A cable tensioner according to claim 1, further comprising:
a tension gauge indicating an amount of tension applied to the cable.

14. A cable tensioner according to claim 13, further comprising:
a spring coupled between said tube and said tension gauge, wherein displacement of said spring is related to said amount of applied tension.

15. A cable tensioner according to claim 1, wherein:
said cable tension lock includes a cam lock that acts on the cable.

16. A cable tensioner for applying tension to a cable relative to a plate or cable securing structure, said cable tensioner comprising:
   a) a tube having a proximal end and a distal end;
   b) a handle coupled to said proximal end of said tube and having a movable portion and a stationary portion, said movable portion rotatable about a first axis relative to said stationary portion, said handle defining a cable passage that has a second axis transverse to said first axis, wherein said handle is configured to receive said cable along the second axis, and wherein rotation of said movable portion relative to said stationary portion operates to pull the cable within said cable passage into tension;
   c) a spring coupled between said proximal end of tube and a distal end of said handle, wherein displacement of said spring is related to said amount of applied tension;
   d) a tension gauge coupled to said spring and between said spring and said distal end of said handle, said tension gauge indicating an amount of tension applied to the cable; and
   e) a cable tension lock that locks an applied tension on the cable.

17. A cable tensioner according to claim 16, wherein:
said spring, said tension gauge, and said cable tension lock are together separable from said handle.

18. A cable tensioner for applying tension to a cable relative to a plate or cable securing structure, said cable tensioner comprising:
   a) a tube having a proximal end and a distal end; and
   b) a gearbox coupled to said proximal end of said tube, said gearbox including, a worm screw, a drive gear in engagement with said worm screw, and a cable pulley rotationally fixed to said drive gear and rotatable about a pulley axis, said cable pulley including structure to engage the cable and having a tubular shaft, a knob coupled relative to said pulley and threadedly engaged to said tubular shaft, wherein rotation of said knob in one direction operates to increase resistance on said pulley, and rotation of said knob in an opposite second direction operates to decrease resistance on said pulley, a cable passage being defined through said drive gear, said tubular shaft of said pulley, and said knob, and transverse to said pulley axis, wherein when the cable is placed through said tube, over said pulley, and through said cable passage, and said tube is advanced over the cable such that said distal end of said tube is contacted against the plate or the cable securing structure with which the cable is used, rotation of said drive gear operates to pull the cable into tension.

\* \* \* \* \*

UNITED STATES PATENT AND TRADEMARK OFFICE
CERTIFICATE OF CORRECTION

PATENT NO. : 9,707,025 B2
APPLICATION NO. : 13/778272
DATED : July 18, 2017
INVENTOR(S) : Cesare Cavallazzi It is certified that error appears in the above-identified patent and that said Letters Patent is hereby corrected as shown below:

On the Title Page

In item (56), in "References Cited", in Column 2, Line 1, after "DOCUMENTS", insert:
--¶3,552,389 1/1971 Allgower et al.--

In item (56), in "References Cited", in Column 2, Line 4, after "606/103", insert:
--¶6,007,538 12/1999 Levin
6,030,410 2/2000 Zurbrugg
6,045,572 4/2000 Johnson
6,200,318 3/2001 Har-shai et al.
6,217,580 4/2001 Levin
6,540,769 4/2003 Miller III
6,712,821 3/2004 Gabbay
6,872,210 3/2005 Hearn
6,969,398 11/2005 Stevens et al.
7,229,444 6/2007 Boyd--

In item (56), in "References Cited", in Column 2, Line 5, after "606/74", insert:
--¶7,255,701 8/2007 Allen et al.
7,299,561 11/2007 Castaneda
7,651,498 1/2010 Shifrin et al.
7,704,252 4/2010 Albertson et al.
7,785,355 8/2010 Mohr et al.
7,935,123 5/2011 Fanger et al.
7,935,126 5/2011 Orbay et al.--

In item (56), in "References Cited", in Column 2, Line 6, after "606/103", insert:
--¶8,192,472 6/2012 Sixto Jr. et al.
8,313,517 11/2012 Mohr et al.

Signed and Sealed this
Twelfth Day of June, 2018

Andrei Iancu
*Director of the United States Patent and Trademark Office*

8,337,497 12/2012 Deslauriers et al.
8,366,754 2/2013 Teague et al.
8,372,123 2/2013 Smisson et al.
8,419,736 4/2013 Albertson et al.
8,425,572 4/2013 Grevious
8,460,295 6/2013 McClellan et al.--

In item (56), in "References Cited", in Column 2, Line 7, after "606/103", insert:
--¶8,486,114 7/2013 Gillard et al.
8,496,659 7/2013 Fernandez
8,556,948 10/2013 Teague et al.
8,668,697 3/2014 Deslauriers et al.
8,679,122 3/2014 Bernstein et al.
8,734,492 5/2014 Mohr et al.
8,740,915 6/2014 Niederberger et al.
8,758,348 6/2014 McClellan et al.
8,758,417 6/2014 Anderson et al.
8,876,824 11/2014 Hearn
8,888,791 11/2014 Jaramillo et al.
8,936,628 1/2015 Anderson
8,974,457 3/2015 McClellan et al.
8,992,530 3/2015 Madjarov
9,023,058 5/2015 Jaramillo et al.
9,055,984 6/2015 Albertson et al.
9,084,644 7/2015 Knueppel
9,084,645 7/2015 Knueppel
9,113,975 8/2015 McClellan et al.
9,173,693 11/2015 McDaniel et al.
9,179,943 11/2015 Blain
9,237,910 1/2016 Seykora et al.
9,237,912 1/2016 Fernandez
9,237,913 1/2016 Gillard et al.
9,241,748 1/2016 Bernstein et al.
9,265,544 2/2016 Waizenegger et al.
9,295,507 3/2016 Albertson et al.
9,402,610 8/2016 Pell et al.
9,421,050 8/2016 Bernstein et al.--

In item (56), in "References Cited", in Column 2, Line 8, after "606/103", insert:
--¶20100069966 3/2010 Castaneda et al.
20100262194 10/2010 Wagner et al.
20120095466 4/2012 Winslow et al.
20150018830 A1 1/2015 Knoepfle et al.
20150305792 A1 10/2015 Knueppel
20160128749 A1 5/2016 Bernstein et al.
20160199111 A1 7/2016 Knoepfle et al.

20170035476 A1 2/2017 Cavallazzi et al.
OTHER PUBLICATIONS
Cable-Ready Cable Grip System Bone Plate, J. Jennings et al., Research Laboratories of Zimmer, Inc., 1997.
Cable System. For Orthopaedic Trauma Surgery, Technique Guide, Synthes, 2011.
Dall-Miles Cable System Surgical Protocol, Stryker, 2007.
Dall-Miles Recon and Trauma Cable System Surgical Protocol, Stryker, 2007.
Fixation of a Periprosthetic Humeral Fracture with CCG-Cable System, L. De Smet et al., Dept. of Orthopaedic Surgery, Acta chir belg, 2005, 105, 543-544.
Locking Attachment Plate. For Treatment of Periprosthetic Fractures, Technique Guide, Synthes, 2009.
NCB Periprosthetic Femur Plate System, Surgical Technique, Zimmer, 2012.
Super Cable Grip and Plate System, Surgical Technique, B00161A, Kinamed, Inc. 2008.
Cable Tensioner with Pistol Grip. Part of the Synthes Orthopaedic Cable System., Synthes, 2011.
LCP Periprosthetic System. Part of the Synthes Locking Compression Plate (LCP) System, Synthes, 2005.
Basic Percutaneous Instrument Set. For 4.5 mm LCP Condylar Plates, Technique Guide, Synthes, 2005.
"U.S. Appl. No. 15/332,616, Final Office Action mailed Mar. 10, 2017", 6 pgs.
"U.S. Appl. No. 15/332,616, Response filed Feb. 16, 2017 to Non Final Office Action mailed Dec. 28, 2016", 9 pgs.--

In the Claims

In Column 22, Line 29, in Claim 2, delete "A" and insert --The-- therefor

In Column 22, Line 36, in Claim 3, delete "A" and insert --The-- therefor

In Column 22, Line 39, in Claim 4, delete "A" and insert --The-- therefor

In Column 22, Line 42, in Claim 5, delete "A" and insert --The-- therefor

In Column 22, Line 45, in Claim 6, delete "A" and insert --The-- therefor

In Column 22, Line 48, in Claim 7, delete "A" and insert --The-- therefor

In Column 22, Line 50, in Claim 8, delete "A" and insert --The-- therefor

In Column 22, Line 55, in Claim 9, delete "A" and insert --The-- therefor

In Column 22, Line 59, in Claim 10, delete "A" and insert --The-- therefor

In Column 22, Line 61, in Claim 11, delete "A" and insert --The-- therefor

CERTIFICATE OF CORRECTION (continued)
U.S. Pat. No. 9,707,025 B2

In Column 22, Line 64, in Claim 12, delete "A" and insert --The-- therefor

In Column 23, Line 3, in Claim 13, delete "A" and insert --The-- therefor

In Column 23, Line 7, in Claim 14, delete "A" and insert --The-- therefor

In Column 23, Line 13, in Claim 15, delete "A" and insert --The-- therefor

In Column 24, Line 7, in Claim 17, delete "A" and insert --The-- therefor